US012714684B2

(12) United States Patent
Domínguez Chávez et al.

(10) Patent No.: US 12,714,684 B2
(45) Date of Patent: Aug. 25, 2026

(54) COMPOUNDS COMPRISING CURCUMIN AND BASIC AMINO ACIDS

(71) Applicant: ALPARIS, S.A. DE C.V., Mexico City (MX)

(72) Inventors: Jorge Guillermo Domínguez Chávez, Veracruz (MX); Karina Mondragón Vásquez, Veracruz (MX); Juan Pablo Senosiain Peláez, Mexico City (MX)

(73) Assignee: ALPARIS, S.A. DE C.V., Mexico City (MX)

( * ) Notice: Subject to any disclaimer, the term of this patent is extended or adjusted under 35 U.S.C. 154(b) by 1015 days.

(21) Appl. No.: 17/640,694

(22) PCT Filed: Jul. 31, 2020

(86) PCT No.: PCT/IB2020/057240
§ 371 (c)(1),
(2) Date: Mar. 4, 2022

(87) PCT Pub. No.: WO2021/044231
PCT Pub. Date: Mar. 11, 2021

(65) Prior Publication Data

US 2022/0370391 A1 Nov. 24, 2022

(30) Foreign Application Priority Data

Sep. 6, 2019 (MX) .................... MX/a/2019/010692

(51) Int. Cl.
*A61K 31/197* (2006.01)
*A61K 31/12* (2006.01)

(52) U.S. Cl.
CPC ............ *A61K 31/197* (2013.01); *A61K 31/12* (2013.01)

(58) Field of Classification Search
None
See application file for complete search history.

(56) References Cited

U.S. PATENT DOCUMENTS

| | | | |
|---|---|---|---|
| 6,475,530 | B1 | 11/2002 | Kuhrts |
| 2014/0031403 | A1 | 1/2014 | Gately et al. |

FOREIGN PATENT DOCUMENTS

| | | | |
|---|---|---|---|
| CN | 107519219 | A | 12/2017 |
| EP | 3437638 | A1 | 2/2019 |
| WO | 2012138907 | A2 | 10/2012 |
| WO | 2015052568 | A2 | 4/2015 |
| WO | 2015085351 | A1 | 6/2015 |
| WO | 2017187302 | A1 | 11/2017 |

OTHER PUBLICATIONS

Bastos et al. Production of Co-Amorphous Materials with Therapeutic Activity. 2017. Retrieved from the Internet on Mar. 24, 2025, https://www.academia.edu/102762436/Production_of_co_amorphous_materials_with_therapeutic_activity?uc-sb-sw=34559437 (Year: 2017).*

Katsuhiko Yamamoto, Taro Kojima, Masatoshi Karashima, Yukihiro Ikeda, Physicochemical Evaluation and Developability Assessment of Co-amorphouses of Low Soluble Drugs and Comparison to the Co-crystals, Chemical and Pharmaceutical Bulletin, 2016, vol. 64, Issue 12, pp. 1739-1746, 2016 (Year: 2016).*

A. Nangia, Indian Patent Application No. 3190/CHE/2010, filing date Oct. 27, 2010, publication date Jul. 13, 2012, Novel Polymorphs and Cocrystals of Curcumin. (81 pages).

K.S. Parvathy, et al., "Curcumin-amino acid conjugates: Synthesis, antioxidant and antimutagenic attributes", Food Chemistry, 2010, pp. 523-530, vol. 120.

M. Puig et al., "Pathophysiology, treatment and experimental models of rheumatoid arthritis" Cuban Journal of Pharmacy, 2011, pp. 297-308, vol. 45, No. 2, with English Translation.

International Search Report (PCT/ISA/210) with translation and Written Opinion (PCT/ISA/237) mailed on May 5, 2021, by the European Patent Office as the International Searching Authority for International Application No. PCT/IB2020/057240. (12 pages).

Written Opinion of the International Preliminary Examining Authority (PCT/IPEA/408) issued by the European Patent Office as the International Searching Authority for International Application No. PCT/IB2020/057240. (8 pages).

Goud et al. Fast dissolving eutectic compositions of curcumin. International Journal of Pharmaceutics (Kidlington), vol. 439, No. 1-2, pp. 63-72, ISSN 0378-5173 (print) ISSN 1873-3476(electronic), Dec. 15, 2012.

Karagianni et al. Co-Amorphous Solid Dispersions for Solubility and Absorption Improvement of Drugs: Composition, Preparation, Characterization and Formulations for Oral Delivery, Pharmaceutics, vol. 10, No. 3, pages Article No. 98, ISSN 1999-4923(print) ISSN 1999-4923 (electronic), Aug. 31, 2018.

Hancock et al., "Characteristics and Significance of the Amorphous State in Pharmaceutical Systems", Journal of Pharmaceutical Sciences, Jan. 1997, pp. 1-12, vol. 86, No. 1.

Shi et al., "Advances in Coamorphous Drug Delivery Systems", Acta Pahrmaceutica Sinica B, 2019, pp. 19-35, vol. 9, No. 1.

* cited by examiner

*Primary Examiner* — Lauren Wells
(74) *Attorney, Agent, or Firm* — Buchanan Ingersoll & Rooney PC

(57) ABSTRACT

The present disclosure relates to: a solid compound formed by curcumin and arginine, which includes molar ratios between 5:1 and 1:5, with improved bioavailability properties, and which contains a solid compound comprising curcumin and arginine; the use thereof in complaints of inflammation, pain, stiffness and reduced range of movement, and in complaints that cause disability owing to the presentation of symptoms of pain, inflammation and stiffness and reduced range of movement, among others; and a pharmaceutical composition containing curcumin and L-arginine with a synergic effect in the therapeutic activity of the combination of curcumin and L-arginine, wherein the selected ratio allows a synergic effect in the therapeutic activity thereof to be obtained, and wherein an exemplary preferred ratio of curcumin to L-arginine is between 5:1 to 1:5.

4 Claims, 20 Drawing Sheets

COMPOUNDS COMPRISING CURCUMIN AND BASIC AMINO ACIDS

FIELD OF THE INVENTION

The present invention refers to co-amorphous and co-crystalline solid compounds of curcumin and arginine with improved physicochemical properties, among others, improved properties of solubility and permeability, resulting in improved bioavailability; as well as compositions containing said solid compound, and the process for preparing the composition and its use.

The present invention also relates to a pharmaceutical combination comprising curcumin with L-arginine and/or pharmaceutically acceptable salts thereof. It also refers to a composition comprising curcumin with L-arginine and/or pharmaceutically acceptable salts thereof, pharmaceutically acceptable vehicles and/or excipients; the process for manufacturing the composition and the use of said composition in conditions requiring analgesic and/or anti-inflammatory activity, the use in pain from moderate to severe, as an antioxidant and as an antitumor agent, among others.

The present invention is a new alternative of therapeutic support as antioxidant, anti-inflammatory agent, analgesic, antitumor agent, antineoplasic agent, among others.

BACKGROUND OF THE INVENTION

Despite the exponential progress in medicine, there is still a need of alternatives for the treatment of conditions where anti-inflammatory, antioxidant, analgesic, antimutagenic or antineoplasic effects, among others are required; such alternatives will have significant effects by helping to solve the problem of disability or reduction in quality of life. Also, alternatives are required to improve recovery and performance in subjects who exercise.

Inflammation has been identified in the development of many diseases and chronic conditions, for example: Alzheimer's disease, Parkinson's disease, multiple sclerosis, epilepsy, brain injury, cardiovascular disease, metabolic syndrome, cancer, allergy, asthma, bronchitis, colitis, arthritis, osteoarthritis, renal ischemia, psoriasis, diabetes, obesity, depression, anxiety, hyperlipidemia, fatigue, AIDS, among others.

Arthritis is a disease that causes inflammation of one or more joints, provoking pain and stiffness. The most common types of arthritis are arthrosis or osteoarthritis, and rheumatoid arthritis. Rheumatoid arthritis follows a fluctuating chronic evolution that causes destruction, deformity and joint disability. It affects about 1% of the world population (Noa Pulg 2011; Physiopathology).

*Curcuma longa* is a plant that belongs to the Zingiberaceae family, whose orange rhizome is used as spice due to its organoleptic properties and is commonly called turmeric.

For a long time, turmeric has been recognized for its medicinal properties; it is of great interest within the medical, scientific and gastronomic world. Most of the benefits of turmeric can be attributed to the antioxidant and anti-inflammatory effects of the curcuminoid compounds.

Curcumin is the main active metabolite of turmeric, its IUPAC name is (1E,6E)-1,7-bis(4-hydroxy-3-methoxyphenyl)-1,6-heptadiene-3,5-dione. There are two tautomeric forms, the keto form which is solid, and the enol form which is liquid.

Curcumin is an orange-yellow solid with a melting point of 183° C., which is soluble in ethanol and in concentrated acetic acid. (Merck Index 15th ed.). It decomposes at high temperatures and is photosensitive.

Curcumin has been recognized to help in the management of different conditions, however, the intake of curcumin alone does not lead to the associated health benefits due to its poor bioavailability, poor absorption, rapid metabolism and rapid elimination.

Due to its low bioavailability and its low or non-existent solubility in water, alternatives for improving these properties have been sought in order to obtain the benefits of curcumin.

Curcumin has different uses around the world and has been combined with various enhancing agents to provide multiple health benefits. In fact, the USFDA (United States Food and Drug Administration) considers it as a GRAS (Generally Recognized as Safe) substance. Clinical studies have demonstrated the tolerability of curcumin from 4000 mg and up to 12,000 mg per day.

To date, several authors mention that curcumin acts through different action mechanisms, one of these being the inhibition of the translocation of the Kappa-β nuclear factor (NFk-β) to the nucleus, which by means of multiple scientific studies has been associated to a number of inflammatory diseases, including cancer, and more recently pulmonary fibrosis.

To mention other mechanisms, it has been reported that curcumin acts at the level of anti-inflammatory mediators, promoting a decrease in the production of pro-inflammatory cytokines such as interleukin 1 beta (IL-1β), interleukin 6 (IL-6), the soluble vascular cell adhesion molecule (sVCAM-1), the soluble CD40 ligand (sCD40L), among others. In addition to the above, curcumin is considered an antioxidant, mainly due to its structure and high degree of unsaturation that allows it to directly trap ROS (reactive oxygen species). It is also able to modulate the expression of proteins that regulate oxidative stress. For example, it increases enzymes that eliminate or substantially reduce ROS and RNS (reactive nitrogen species), as well as superoxide dismutase (SOD), catalase and glutathione peroxidase (GPx) enzymes.

The recommended oral daily dose of curcumin in adults is from 500 mg to 12,000 mg.

Arginine (ARG) is one of the twenty amino acids that form part of proteins and is classified as a semi-essential amino acid.

Arginine participates in the mechanism of nitric oxide synthesis, which causes relaxation of blood vessels (vasodilation).

Arginine is involved in many activities of the endocrine glands, such as the stimulation of the immune function by increasing the number of leukocytes, it has a vasodilator effect. In addition, it is involved in the synthesis of creatine, polyamines, collagen and DNA (deoxyribonucleic acid) production, cholesterol reduction, as well as stimulation of the release of growth hormone, somatotropin.

Like L-carnitine (L-CAR), L-arginine (L-ARG) is considered to enhance functions in the use of fatty acids as energy (muscle fuel). L-arginine may reduce cholesterol thereby improving the capacity of the circulatory system, stimulates growth hormone release, reduces levels of body fat and facilitates the recovery of athletes (resulting from anaerobic exercise) of the muscles and converts it into urea, which is excreted in the urine.

The recommended oral daily dose of L-arginine is from 500 mg to 6,000 mg.

The inventions described in the present application have not been reported in any document of the prior art. Some related documents are:

WO2017187302-Inpha D. Combination consisting of β-sitosterol, oligomeric proanthocyanidins and curcumin, with anti-inflammatory and antiproliferative activity for use in the treatment and prevention of urological disorders. Additionally, the composition includes excipients selected from bromelain, a sucrose ester, arginine base or piperine.

CN107519219 (2017)—Shenzhen. Multivitamin composition containing L-arginine, L-lysine, L-isoleucine, L-amino acid, L-aspartate, L-citrulline, glycine, vitamins B1, B6, B2, B12; folic acid, iron, curcumin extract, melon tea extract, choline, starch, sodium carboxymethyl starch, magnesium stearate.

U.S. Pat. No. 6,475,530 (2000)—Kuhrts H. Composition for producing weight loss initially comprising a thermogenic norepinephrine generating substance that such as ephedrine or Synephrine; a COX-2 inhibitor selected from a botanical derivative such as *Polygonum cupidatum, P. multiflorum, Scutellaria baicalensis*, white willow bark, turmeric, curcumin, rosemary, green tea, holy basil or ginger, and a methylxanthine. Furthermore, the above composition includes a growth hormone-producing compound selected from L-lysine and L-arginine.

IN201003190I4—Crystalline RPL. Solid forms of curcumin form II, form III, amorphous curcumin and cocrystals of curcumin-resorcinol and curcumin-pyrogallol.

WO2012138907A2—Translation G. Solid forms of curcumin with 2-aminobenzimidazole and L-lysine in amorphous form.

WO2015052568A3—Laurus Labs. Solid forms of curcumin with piperazine, nicotinamide, isonicotinamide, naproxen sodium, piperidine; curcumin sodium and form X of curcumin.

SUMMARY OF THE INVENTION

The present invention relates to a combination comprising curcumin and/or its pharmaceutically acceptable salts and L-arginine and/or its pharmaceutically acceptable salts.

The present invention also relates to a composition comprising curcumin with L-arginine and/or their pharmaceutically acceptable salts, vehicles and/or excipients; the process for preparing the composition and the use of said composition in conditions that cause disability due to symptoms of pain, inflammation, swelling, stiffness, decreased range of motion and which require analgesic, anti-inflammatory, antioxidant and antitumor activity, among others.

The present invention also refers to a combination of curcumin and L-arginine wherein the selected ratio allows obtaining a synergistic effect in its therapeutic activity, and wherein the molar ratio of curcumin:L-arginine is between 1:5 to 5:1, wherein the preferred ratio of curcumin:L-arginine is between 1:3 to 3:1, from 1:2 to 2:1.

The composition containing curcumin and L-arginine promotes a faster onset of the anti-inflammatory and analgesic action, compared to curcumin alone, due to the increased dissolution and improved absorption of curcumin.

The present invention refers to a co-amorphous solid and a co-crystalline solid of curcumin and L-arginine with improved therapeutic properties for treating inflammation and hyperalgesia.

The present invention relates to compositions comprising a co-amorphous or co-crystalline solid of curcumin and L-arginine, and pharmaceutically acceptable vehicles and/or excipients; the process for preparing the composition and the use of said composition in conditions that require analgesic, anti-inflammatory, antioxidant and antitumor activity, among others.

The present invention also relates to a co-amorphous or co-crystalline solid of curcumin and L-arginine that shows enhanced solubility properties than curcumin, which results in an increase of its absorption and favors its concentration.

Based on studies using models of inflammation and hyperalgesia, it may be considered that pharmacokinetic processes (absorption) and pharmacodynamic processes that favor the potentiation of the analgesic and anti-inflammatory effect of curcumin and L-arginine, are modified.

The present invention relates to an amorphous solid compound with improved properties comprising curcumin and an organic compound as co-former selected from the group consisting of arginine, alanine, glycine, lysine, histidine, azelaic acid, pimelic acid, 2,4-dihydroxybenzoic acid, 3,5-dihydroxybenzoic acid, 3,4-dihydroxybenzoic acid, 3,4,5-trihydroxybenzoic acid, malonic acid, oxalic acid, and picolinamide. When the co-former is an amino acid, it may have the L-configuration, the D-configuration, or it may be a DL-racemic mixture.

The method used to prepare the new solid forms of the present invention is selected from the group consisting of slurry, flash evaporation, and mechanochemical reaction.

The inventions of the present invention reduce the adverse effects of nonsteroidal anti-inflammatory drugs (NSAIDs) and opioids by using different mechanisms of action to provide analgesic, anti-inflammatory, antioxidant and anti-tumor activity, among others.

The inventions of the present application constitute a valuable tool in the control of pain and inflammation, with the advantage of reducing the consumption of NSAIDs or opioids and other compounds that may cause gastric damage, gastric ulcers, severe reactions of cell damage and hepatic damage.

BRIEF DESCRIPTION OF THE FIGURES

The figures illustrate the characterization of the solids obtained and the performance of the invention when administered to the study subjects.

FIG. 1*a* corresponds to the temporary profile and FIG. 1*b* shows areas under the curve (AUC) (−1 h means administration 1 hour before).

FIG. 2*a* corresponds to the temporary profile and FIG. 2*b* shows the areas under the curve (AUC).

FIG. 3*a* corresponds to the temporary profile and FIG. 3*b* shows the areas under the curve (AUC).

FIG. 4*a* corresponds to the temporary profile and FIG. 4*b* shows the areas under the curve (AUC).

FIG. 5*a* corresponds to the temporary profile and FIG. 5*b* shows the areas under the curve (AUC).

FIG. 6*a* corresponds to the temporary profile and FIG. 6*b* shows the areas under the curve (AUC).

FIG. 7*a* corresponds to the temporary profile and FIG. 7*b* shows the areas under the curve (AUC).

FIG. 8*a* corresponds to the temporary profile and FIG. 8*b* shows the areas under the curve (AUC).

FIG. 9*a* corresponds to the temporary profile and FIG. 9*b* shows the areas under the curve (AUC).

FIG. 10*a* corresponds to the temporary profile and FIG. 10*b* shows the areas under the curve (AUC).

DETAILED DESCRIPTION OF THE INVENTION

Figures 1A, 1B:
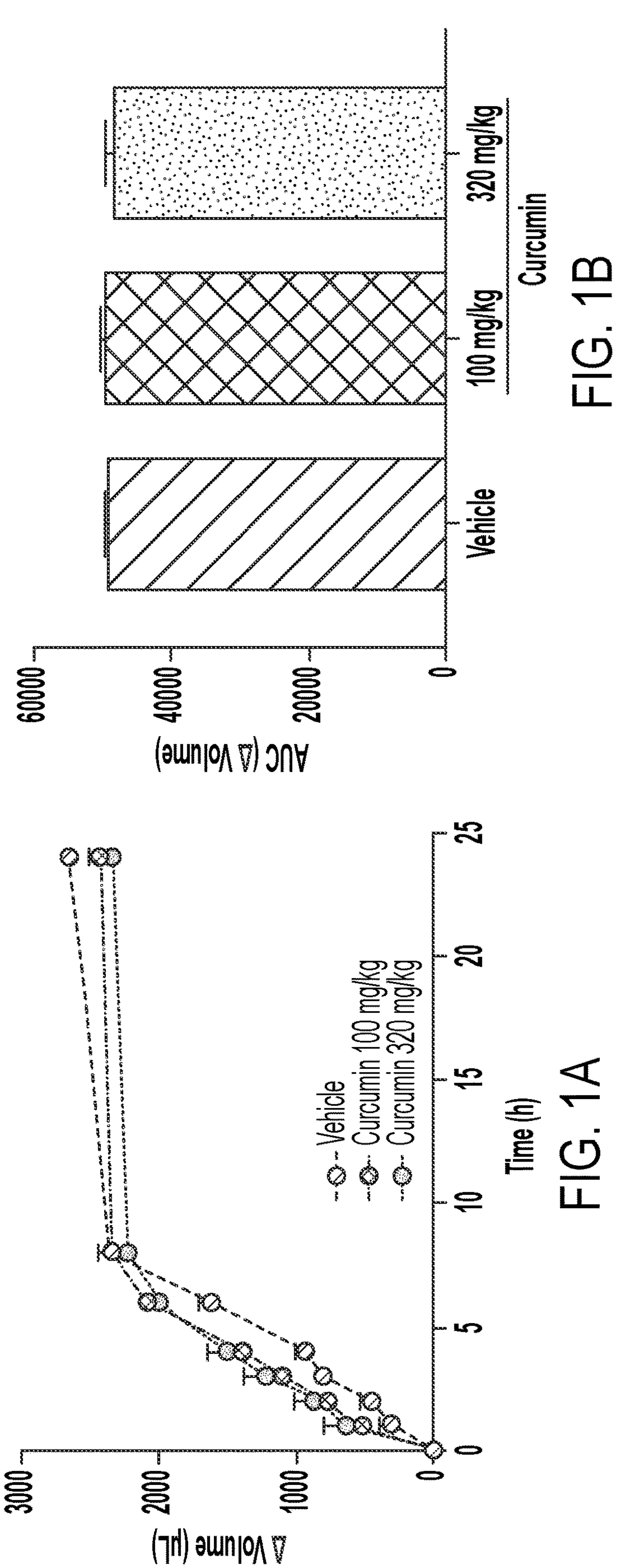
FIGS. 1*a* and 1*b*. Effect produced by oral administration of 100 and 320 mg/kg of curcumin (−1 h) on Complete Freund's Adjuvant (CFA)-induced inflammation.

The present invention provides a combination comprising effective amounts of curcumin and L-arginine with an unexpected anti-inflammatory effect and with other beneficial effects such as pain reduction, wherein the drug ratio curcumin:L-arginine is from 3:1 to 1:3.

On the other hand, it refers to solid co-amorphous and co-crystalline compounds of curcumin and L-arginine with improved properties, and compositions containing sch compounds, as well as the process for preparing the composition and use thereof. It provides a new, valuable tool with enhanced physicochemical properties, such as enhanced solubility properties, resulting in enhanced bioavailability properties.

The present invention is a new alternative therapeutic support as antioxidant, anti-inflammatory, analgesic, antitumor, anticancer agent, among others. It exhibits an invention for the control or suppression of inflammation and pain that decreases or avoids the possible adverse effects of NSAIDs or opioids.

The use of pain models is a way to know the impact of curcumin and L-arginine compounds on the anti-inflammatory effect and even on the antinociceptive effect. Acute pain models use a physical or chemical stimulus with the purpose of determining the response latency of the animal being subjected to said stimulus. With the models, the nociceptive threshold of the animal is objectively determined, so that the obtained parameters are a consequence of the classic mechanism of pain as a reflection within a physiological mark.

By means of preclinical studies, the present invention demonstrates the pharmacodynamic course shown by the curcumin:L-arginine combination.

The localized inflammatory injury in joints may offer an intermediate model of inflammation between acute and chronic, whereas induction of generalized arthritis with Freund's adjuvant (CFA) is a model of chronic inflammation.

The carrageenan (CAR)-induced subplantar edema model was used in the evaluation of the acute effect.

Various methods have been developed to examine the anti-inflammatory properties of drugs in laboratory animals such as rodents. Each of these methods involves exerting a potentially painful (nociceptive) stimulus, followed by the measurement of a clearly observable response.

Preclinical studies were performed in rats with a chronic inflammation model using complete Freund's adjuvant (CFA) given intra-articularly (AIA), as well as an acute model induced by carrageenan (CAR) given in the subplantar region.

Preclinical Study Using Complete Freund's Adjuvant (CFA) Model

In the assessment of the pharmacological interaction, it must be considered that when two drugs are administered together, it is necessary to characterize the effect of the combination with respect to the individual effect of each drug, as shown in the figures.

The time course of the anti-inflammatory effect produced by orally administered curcumin alone, L-arginine alone and the co-amorphous solid compound of curcumin and L-arginine, was obtained in the complete Freund's adjuvant (CFA)-induced arthritis model by the intra-articular route (AIA) in Sprague-Dawley male rats (n=6).

The complete Freund's adjuvant (chronic inflammation) model and the carrageenan (acute inflammation) model were used for evaluating the possible anti-inflammatory effect of curcumin (FIGS. 1*a*, 1*b*, 2*a* and 2*b*), L-arginine (FIGS. 3*a*, 3*b*, 4*a* and 4*b*) or the co-amorphous compound of curcumin and L-arginine in a 1:2 ratio (FIGS. 5*a*, 5*b*, 6*a*, 6*b*).

Figures 2A, 2B:
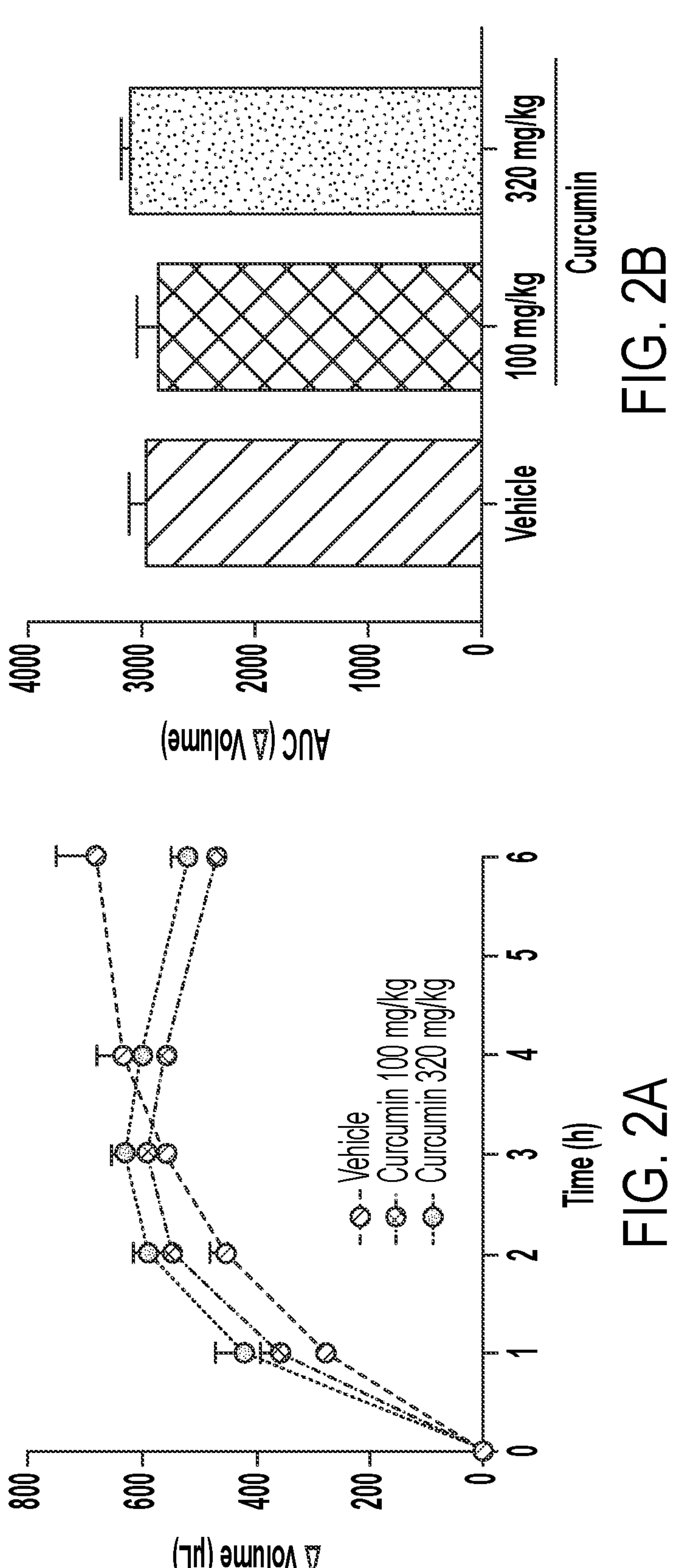
FIGS. 2*a* and 2*b*. Effect produced by oral administration of 100 and 320 mg/kg of curcumin (−1 h) on carrageenan (CAR)-induced inflammation.
Figure 3B:
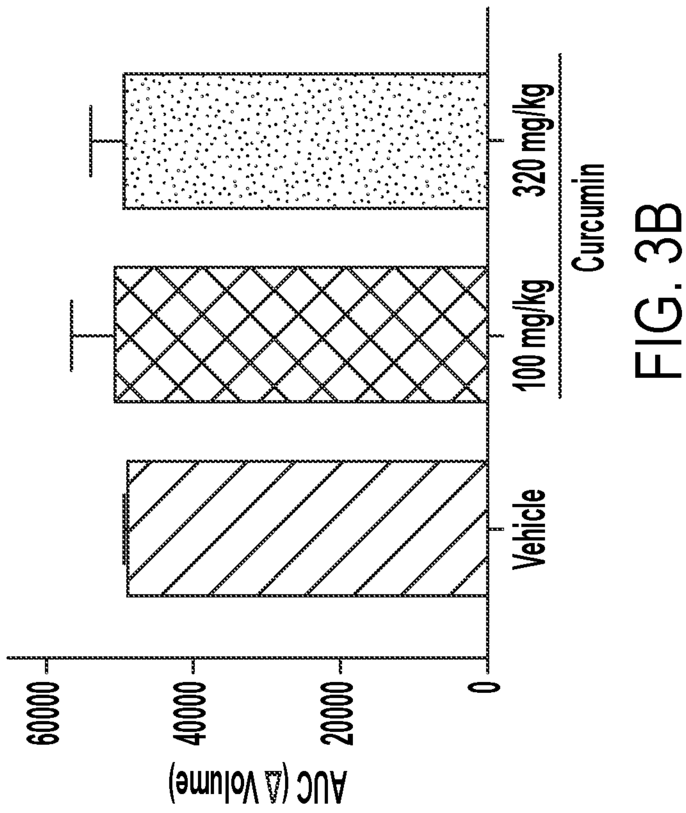
FIGS. 3*a* and 3*b*. Effect produced by oral administration of 100 and 320 mg/kg of L-arginine (−1 h) on CFA-induced inflammation.
Figure 3A:
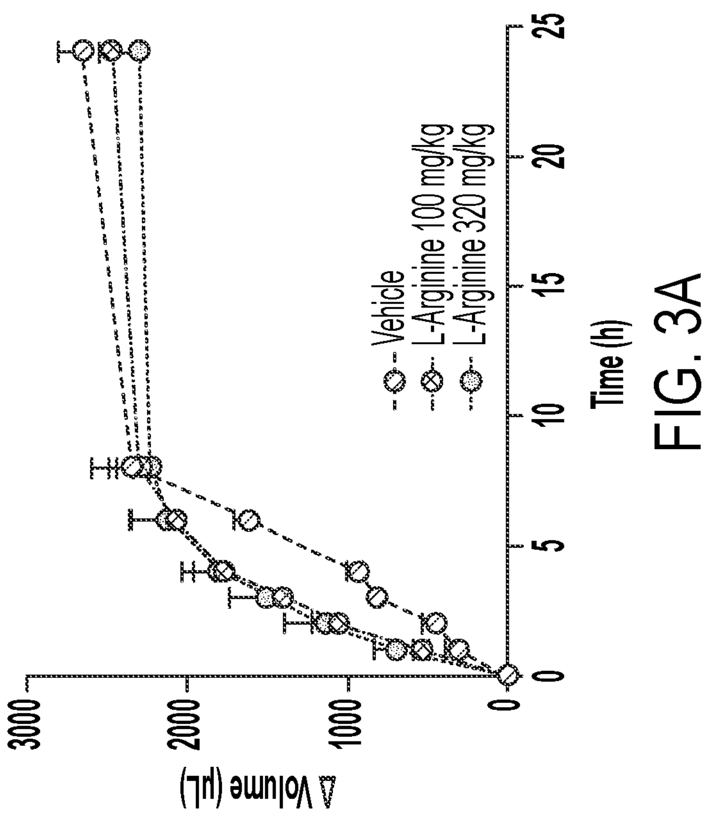

In these models, the inflammation induced by the complete Freund's adjuvant and carrageenan is determined by the volume displacement measured with a plethysmometer. FIGS. 1*a*, 1*b*, 2*a* and 2*b* show that orally administered curcumin (100-320 mg/kg) is unable to reverse the inflammatory effect induced by complete Freund's adjuvant (FIG. 1*b*) or carrageenan (FIG. 2*b*). It can even be observed that curcumin shows an inflammatory effect with respect to the vehicle at 3 and 4 hours employing the 100 mg/kg dose, and between 2 and 6 hours employing the 320 mg/kg dose in the complete Freund's adjuvant model (FIG. 1*a*). The same phenomenon is observed with curcumin 320 mg/kg in the carrageenan model at 1 and 2 hours of evaluation. However, the two doses of curcumin (100 and 320 mg/kg) that were assessed in this model seem to reverse the inflammatory effect induced by carrageenan at 6 hours (FIG. 2*a*).

Figure 4B:
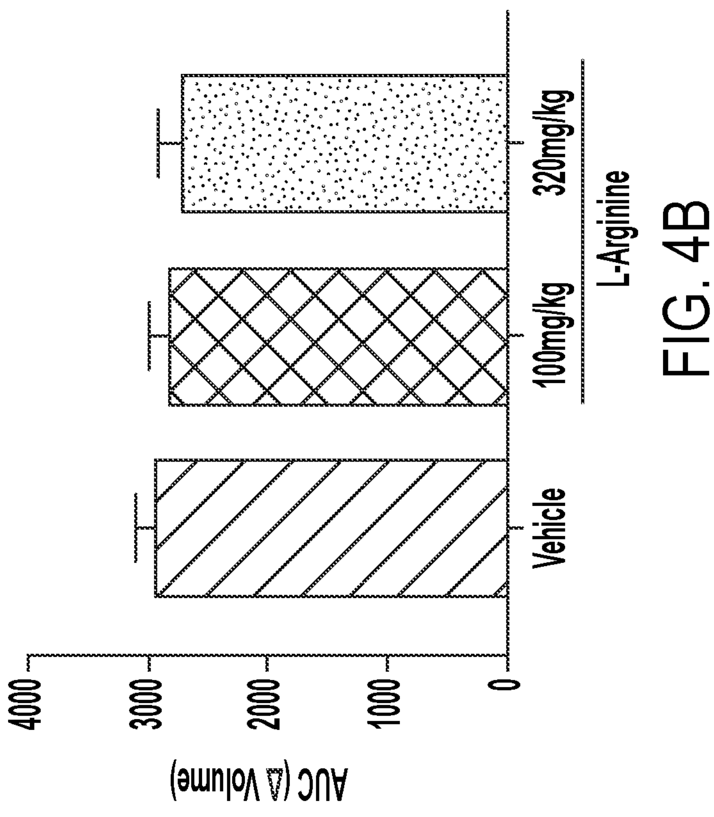
FIGS. 4*a* and 4*b*. Effect produced by oral administration of 100 and 320 mg/kg of L-arginine (−1 h) on CAR-induced inflammation.
Figure 4A:
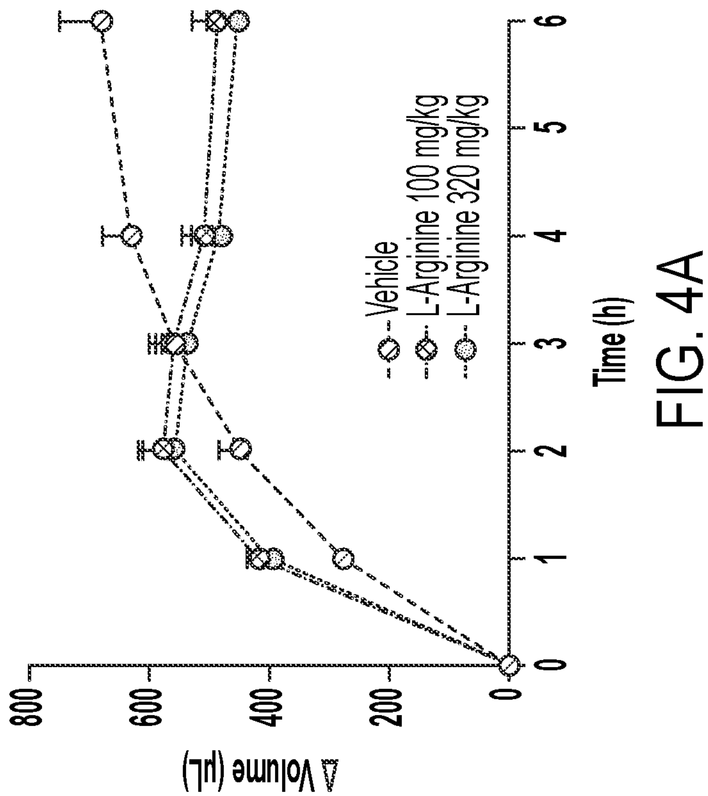

FIGS. 3*a*, 3*b*, 4*a* and 4*b* show that, just like curcumin, oral L-arginine at the assessed doses (100 and 320 mg/kg), was not able to reverse the inflammatory effect induced by the complete Freund's adjuvant (FIG. 3*b*) or carrageenan (FIG. 4*b*). On the contrary, L-arginine showed an inflammatory effect in relation to the vehicle between 2 and 4 hours of the assessment in the complete Freund's adjuvant model (FIG. 3*a*), whereas in the carrageenan model, L-arginine was inclined to show a proinflammatory effect during the first two hours of the assessment, however, at 4 and 6 hours of evaluation (FIG. 4*a*).

Figure 5B:
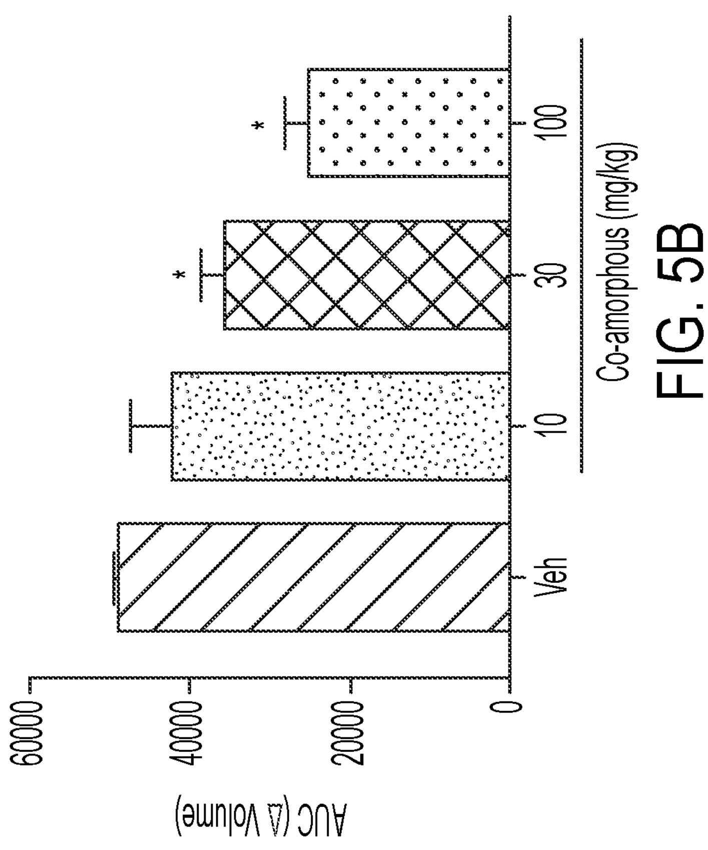
FIGS. 5*a* and 5*b*. Anti-inflammatory effect of oral administration of 10, 30 and 100 mg/kg of the co-amorphous formed by curcumin and L-arginine (ratio 1:2, −1 h) on the Complete Freund's Adjuvant (CFA) model.
Figure 5A:
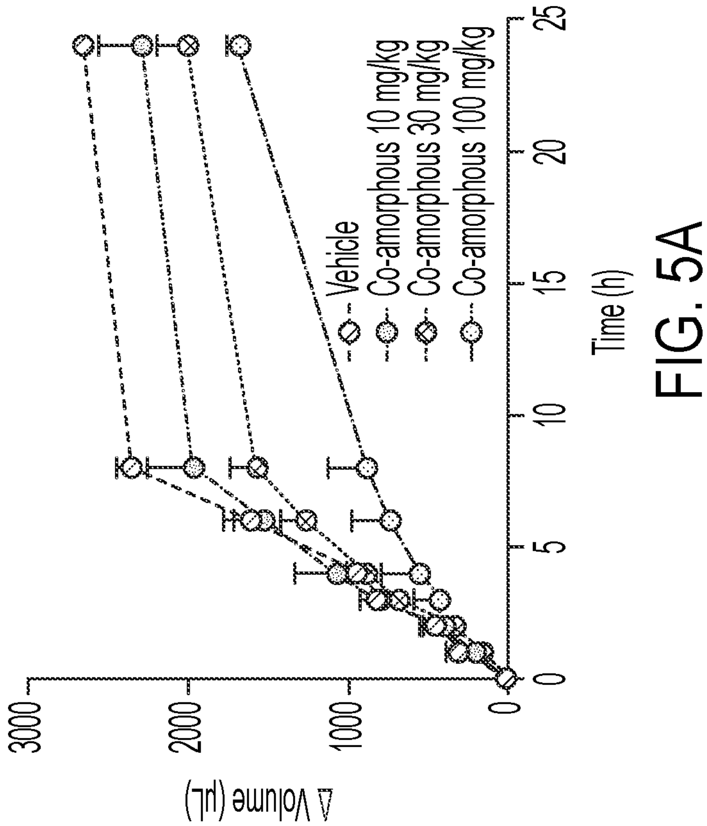
Figure 6B:
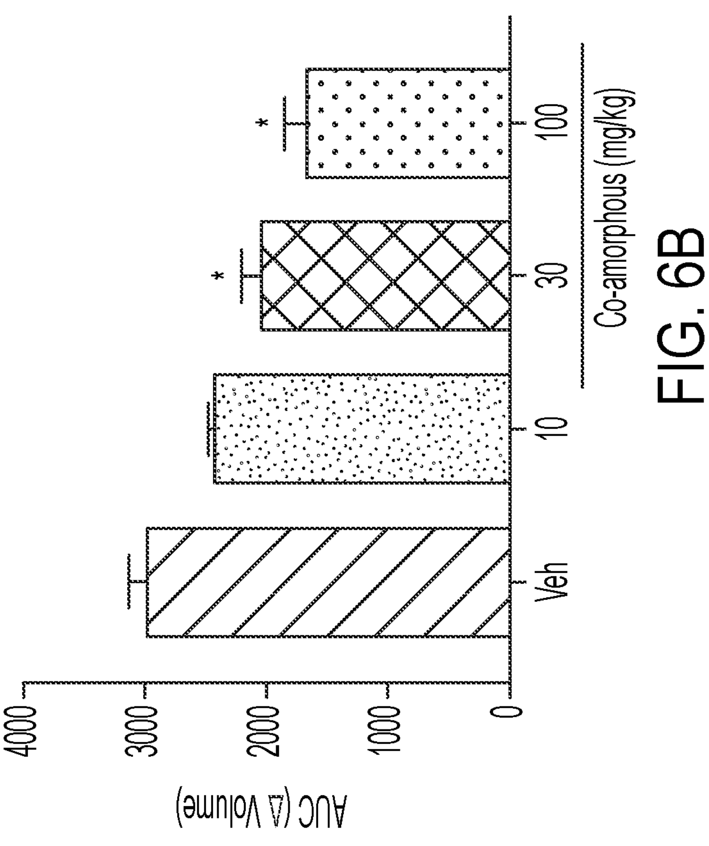
FIGS. 6*a* and 6*b*. Anti-inflammatory effect of oral administration of 10, 30 and 100 mg/kg of the co-amorphous formed by curcumin and L-arginine (ratio 1:2, −1 h) on the CAR model.
Figure 6A:
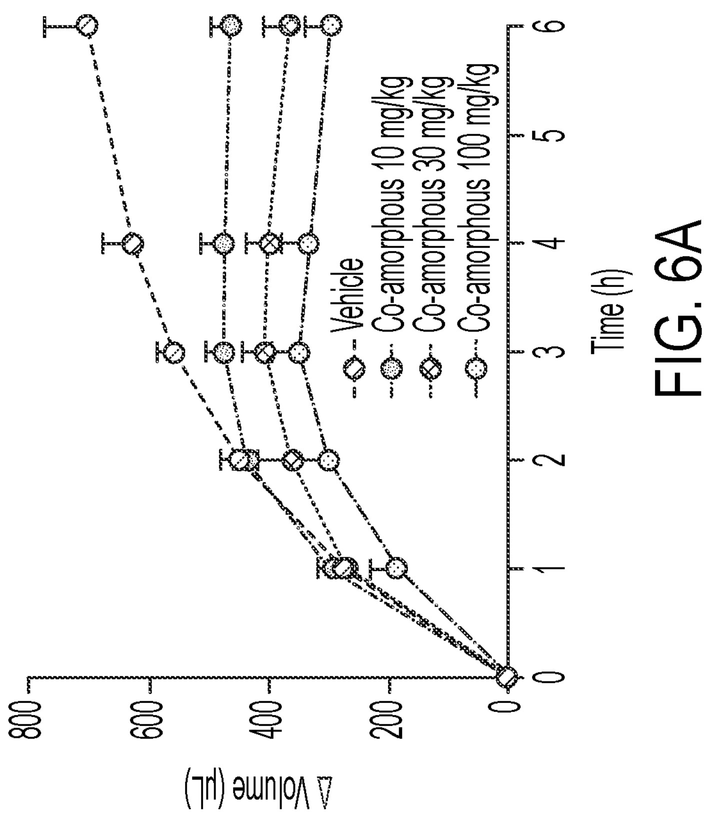

Contrary to the observations with the individual oral administration of curcumin or L-arginine, oral administration of the co-amorphous compound of curcumin and L-arginine 1:2 was able to reverse the inflammation induced by the complete Freund's adjuvant (FIGS. 5*a* and 5*b*) or carrageenan (FIGS. 6*a* and 6*b*) in a dose-dependent and statistically significant way with respect to the vehicle. In both models, the statistical difference with respect to the vehicle was reached at doses of 30 and 100 mg/kg (FIGS. 5*b* and 6*b*). Regarding the time courses, the 30 mg/kg dose reached a statistical difference since the eighth hour, whereas the 100 mg/kg dose was statistically significant with respect to the vehicle as of the sixth hour in the complete Freund's adjuvant model (FIG. 5*a*), while the dose of 10 mg/kg in the carrageenan model was significant since the fourth hour. P value is 0.05.

Additionally, we compared treatments with curcumin, L-arginine, and the co-amorphous compound of curcumin and L-arginine at a fixed dose of 100 mg/kg. In this comparison, only the oral administration of the co-amorphous compound of curcumin and L-arginine was able to significantly reverse the inflammation induced by the complete Freund's adjuvant or carrageenan. In the time courses, as of the sixth hour, the co-amorphous compound of curcumin and L-arginine, but not curcumin or L-arginine individually, reached a statistical difference with respect to the vehicle in the complete Freund's adjuvant model. Regarding the carrageenan model, the co-amorphous compound of curcumin+L-arginine shows an anti-inflammatory effect since the second hour, whereas curcumin or L-arginine reaches this difference only in the last measurement.

Verification of Combination Effectiveness.

Figures 7A, 7B:
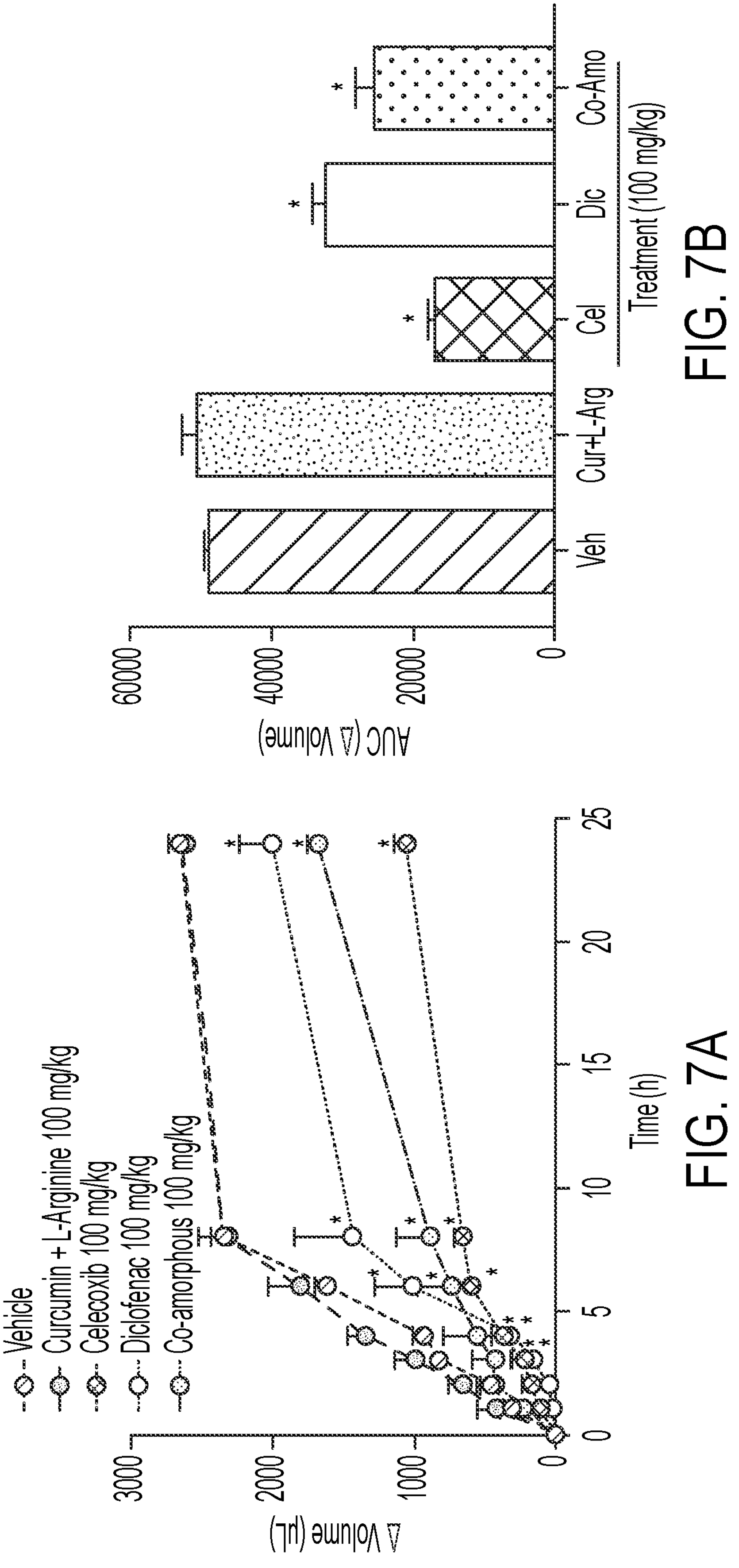
FIGS. 7*a* and 7*b*. Effect produced by oral administration of 100 mg/kg of: the combination curcumin+L-arginine (Cur+L-Arg) in a 1:2 ratio; vehicle (Veh); celecoxib (Cel); diclofenac (Dic); and co-amorphous (Co-amo) formed by curcumin and L-arginine (1:2 ratio), on CFA-induced inflammation.
Figures 8A, 8B:
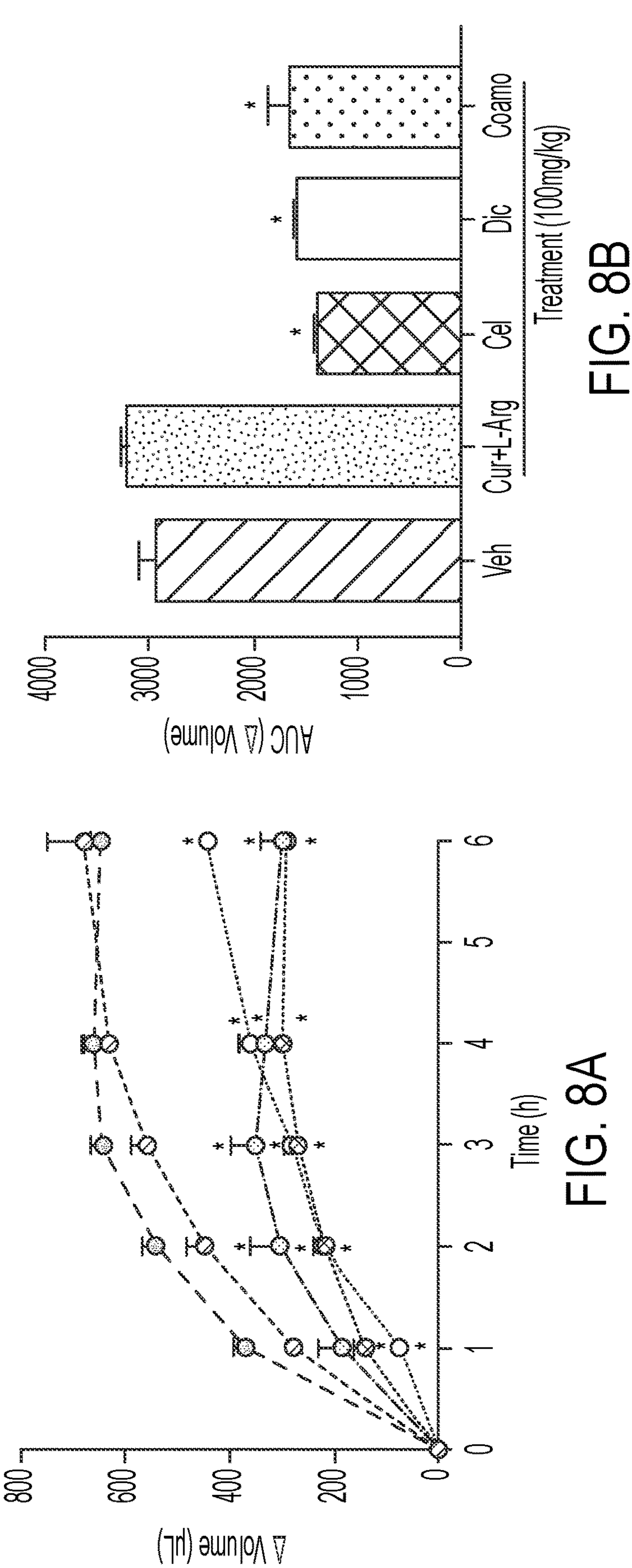
FIGS. 8*a* and 8*b*. Effect produced by oral administration of 100 mg/kg of: the combination curcumin+L-arginine (Cur+L-Arg) in a 1:2 ratio; vehicle (Veh); celecoxib (Cel); diclofenac (Dic); and co-amorphous (Coamo) formed by curcumin and L-arginine (1:2 ratio), on CAR-induced inflammation.

100 mg/kg of the co-amorphous compound of curcumin and L-arginine was compared against 100 mg/kg of a physical mixture of curcumin+L-arginine at a ratio of 1:2 (51.4 mg/kg of curcumin+48.6 mg/kg of L-arginine). FIGS. 7*a*, 7*b*, 8*a* and 8*b* show that the co-amorphous, but not the physical mixture, is capable of reversing the inflammatory effect induced by the complete Freund's adjuvant (FIGS. 7*a* and 7*b*) or carrageenan (FIGS. 8*a*, 8*b*). In addition, it can be observed that both celecoxib and diclofenac (positive controls) exhibited an anti-inflammatory effect at the same dose of 100 mg/kg in both models (FIG. 7*a*, 8*a*). When statistically comparing the treatments with celecoxib, diclofenac, and the co-amorphous compound of curcumin and L-arginine 1:2, there was no statistically significant difference among them, which suggests that the co-amorphous of curcumin and L-arginine 1:2 is as effective as the drugs clinically used for treating conditions that involve an inflammatory process. It is not possible to obtain such result with the physical mixture of curcumin+L-arginine.

Figure 9B:
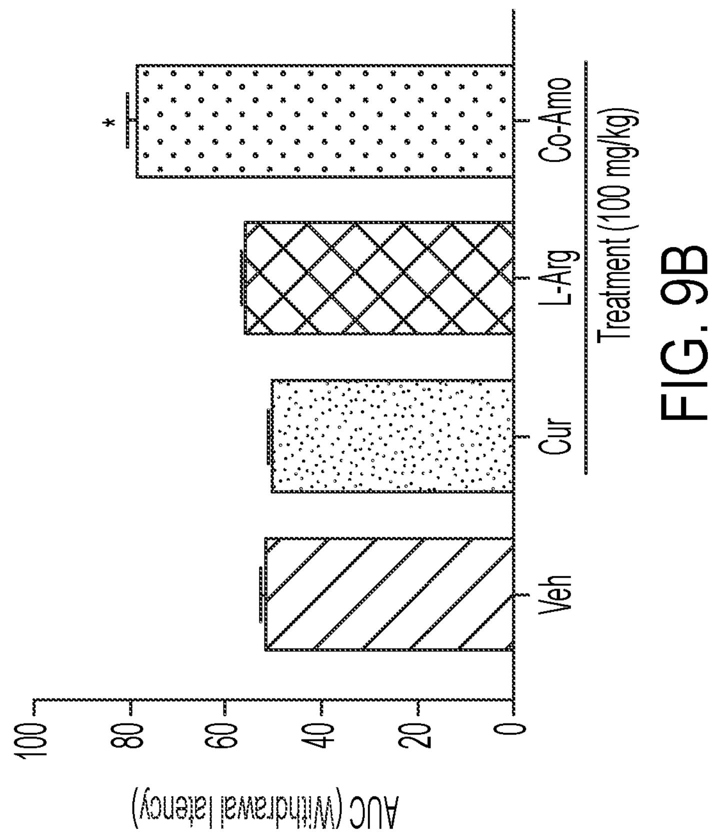
FIGS. 9*a* and 9*b*. Effect produced by oral administration of 100 mg/kg of curcumin (Cur), L-arginine (L-Arg), vehicle (Veh), and co-amorphous (Co-Amo) formed by curcumin and L-arginine (1:2 ratio) on CFA-induced thermal hyperalgesia.
Figure 9A:
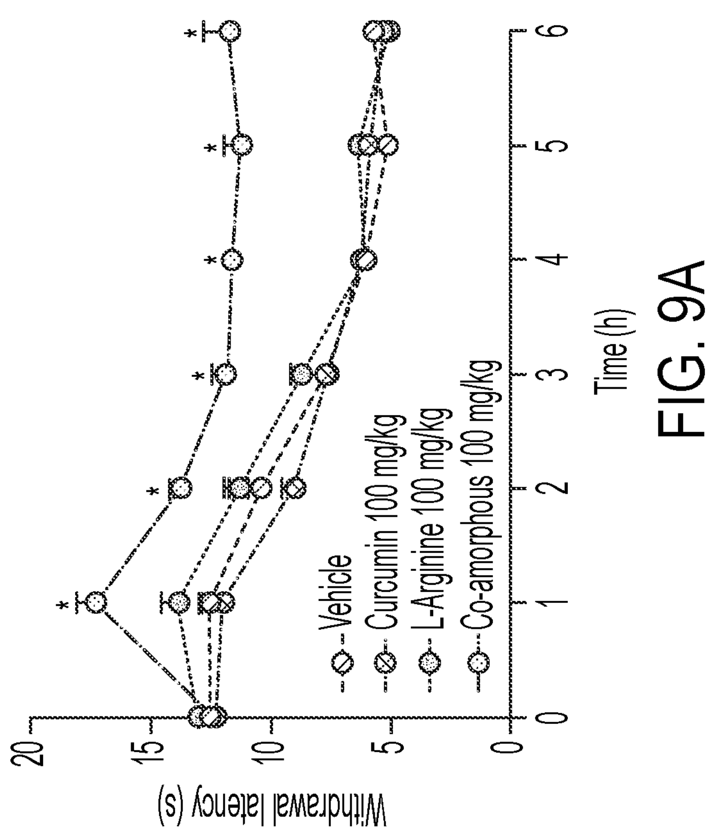
Figure 10B:
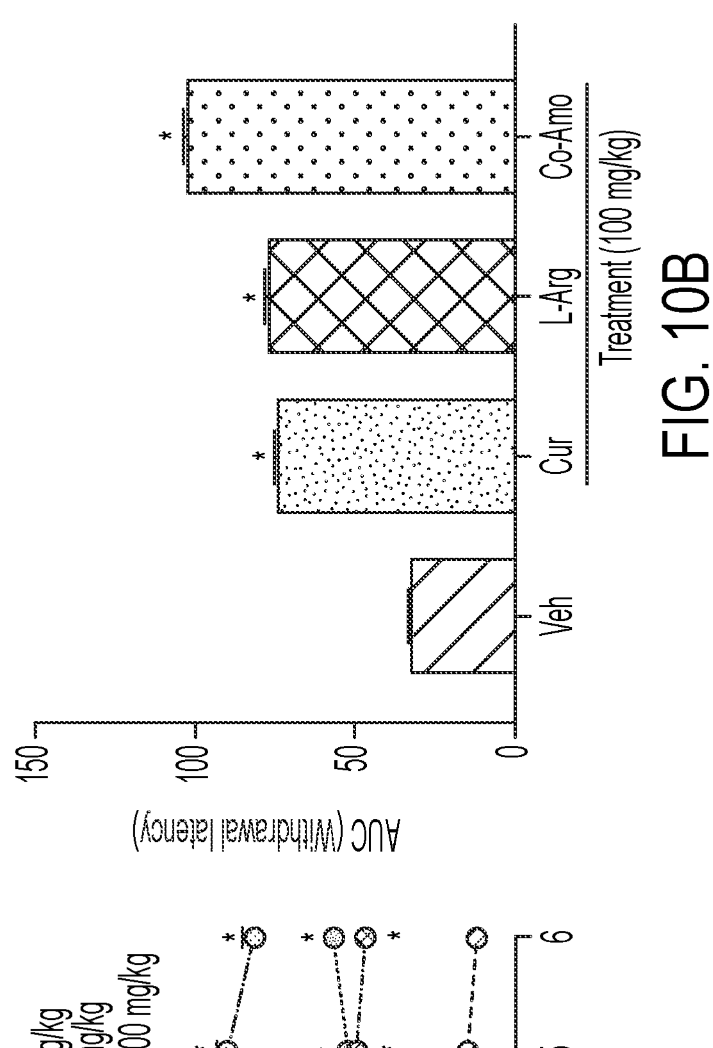
FIGS. 10*a* and 10*b*. Effect produced by oral administration of 100 mg/kg of curcumin (Cur), L-arginine (L-Arg), vehicle (Veh), and co-amorphous (Co-Amo) formed by curcumin and L-arginine (1:2 ratio) on CAR-induced thermal hyperalgesia.
Figure 10A:
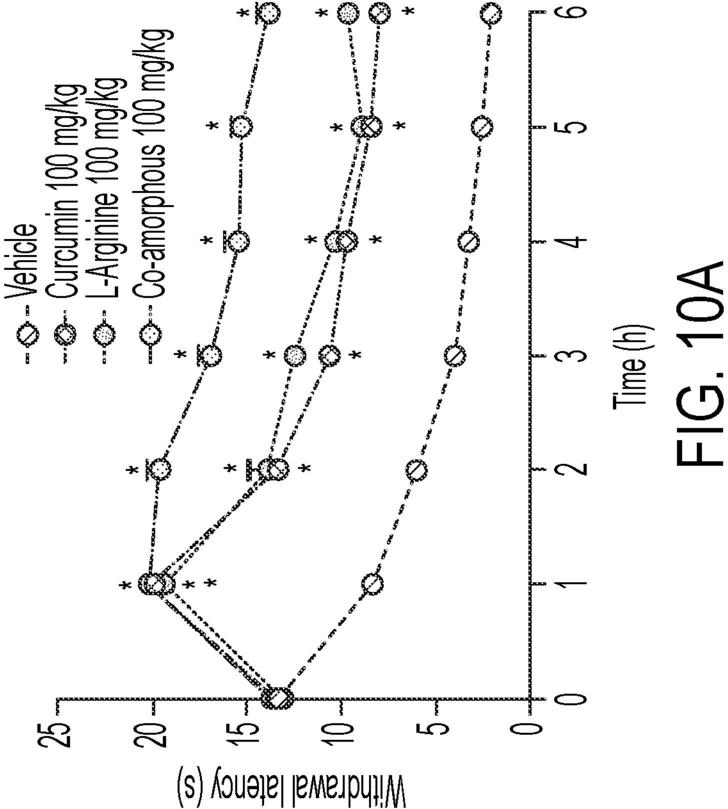

In order to determine whether the co-amorphous compound of curcumin and L-arginine is capable of producing an antihyperalgesic effect, a dose of 100 mg/kg of the co-amorphous compound was assessed in the model of thermal hyperalgesia induced by complete Freund's adjuvant or carrageenan. FIGS. 9*a*, 9*b*, 10*a* and 10*b* show that the co-amorphous of curcumin and L-arginine can produce a statistically significant antihyperalgesic effect in the complete Freund's adjuvant model (FIG. 9*a-b*). In the carrageenan model, the three treatments produce an antihyperalgesic effect, however, the co-amorphous compound provides statistically greater relief for hyperalgesia with respect to the vehicle, curcumin or L-arginine.

Characterization of New Forms of Curcumin and L-Arginine

In the determination of the stoichiometry of the curcumin and L-arginine complex in solution, an absorption spectrum was obtained by the mole ratio method.

Figure 11:
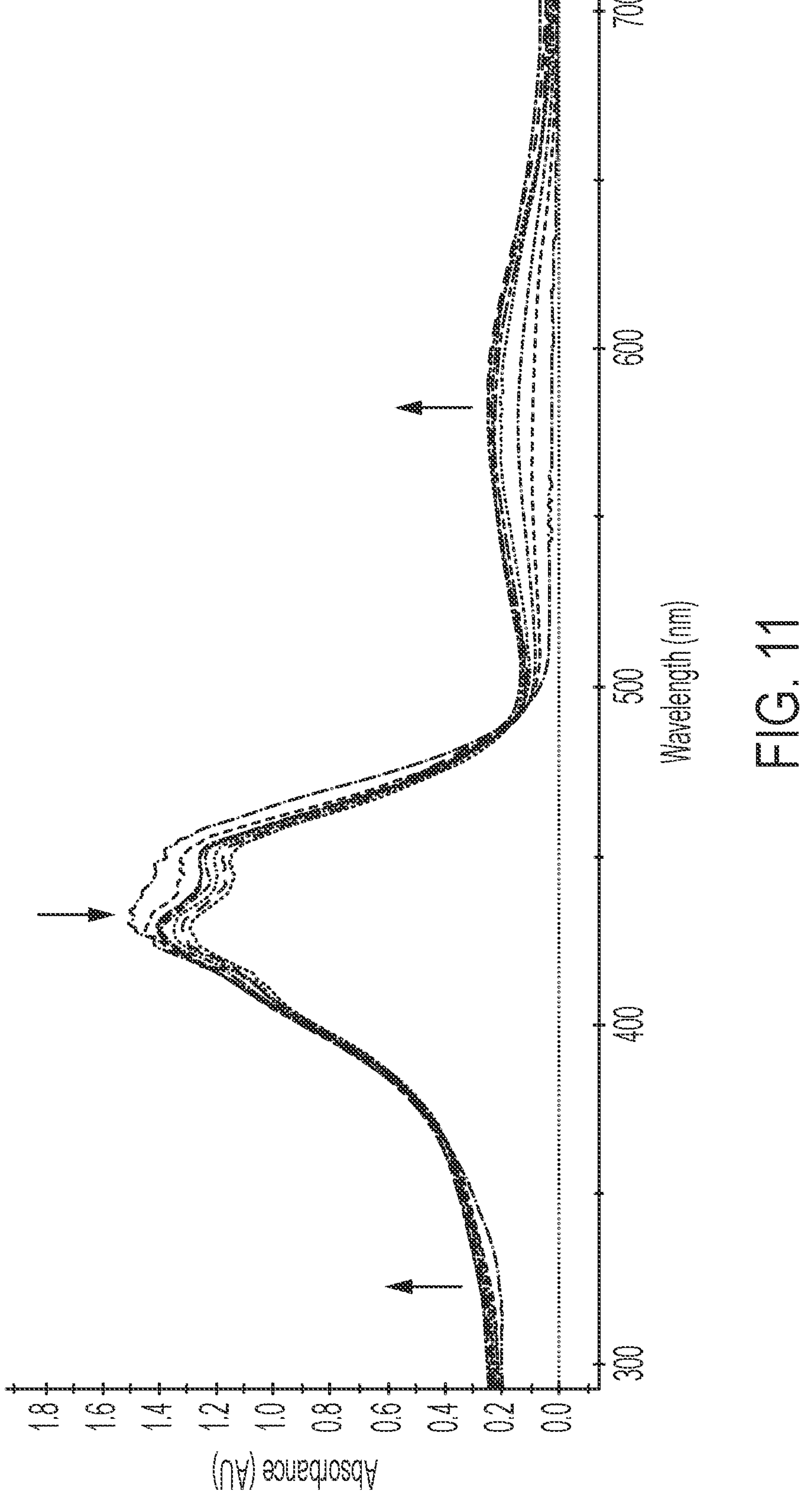
FIG. 11. UV absorption spectrum of a curcumin and L-arginine complex in dimethylsulfoxide solution at different concentrations.

FIG. 11 shows UV absorption spectra obtained for a complex formed by curcumin and L-arginine in dimethylsulfoxide solution at different concentrations. The graph is obtained as follows: Curcumin is placed in dimethylsulfoxide (DMSO) solution, the UV spectrum is obtained and different aliquots of L-arginine (10 μL of a 0.0081M solution) are gradually added, obtaining the UV spectra for each addition. As a result, it is appreciated that the stability and union of the curcumin and L-arginine complex is preserved.

The image shows the absorption spectrum of curcumin at a concentration of 0.000027 M which corresponds to 0.03 absorbance units at 580 nm, and the spectra resulting from the addition of different aliquots of arginine to the curcumin solution. The image shows an absorption band at 580 nm, which is generated and increases with the addition of arginine to the curcumin solution. This absorption band does not correspond to curcumin or L-arginine, which do not exhibit UV-Vis activity at this wavelength, as shown in the raw materials spectra. This suggests that such absorption band corresponds to the formation of a supramolecular curcumin:L-arginine complex in solution. On the other hand, the graph shows the absorption of the curcumin and L-arginine complex at 580 nm as a function of the concentration of L-arginine, wherein the increase in the concentration of arginine favors the formation of a greater amount of the complex and results in increased absorption up to 0.2518 absorbance units, in agreement with the Lambert-Beer law. It is worth mentioning that, with the constant increase of the L-arginine concentration within the curcumin solution, the curcumin interaction sites become saturated and generate a smaller change until saturation, where no significant changes are further observed. According to this graph, the equilibrium constant for the complex formation is 9254.

On the other hand, for the characterization of the obtained solid forms, we analyzed the initial curcumin corresponding to the untreated curcumin, and/or the curcumin subjected to slurry treatment, rapid evaporation or mechanochemical reaction, as well as the untreated co-former.

In the X-ray Powder Diffraction (XRPD) test, the three amorphous phases of curcumin and L-arginine with 1:1, 1:2 and 2:1 stoichiometry exhibit the characteristic form of an amorphous compound.

FT-IR Spectroscopy of the Three Co-Amorphous Phases of Curcumin and L-Arginine with 1:1, 1:2 and 2:1 Stoichiometry.

Figure 12:
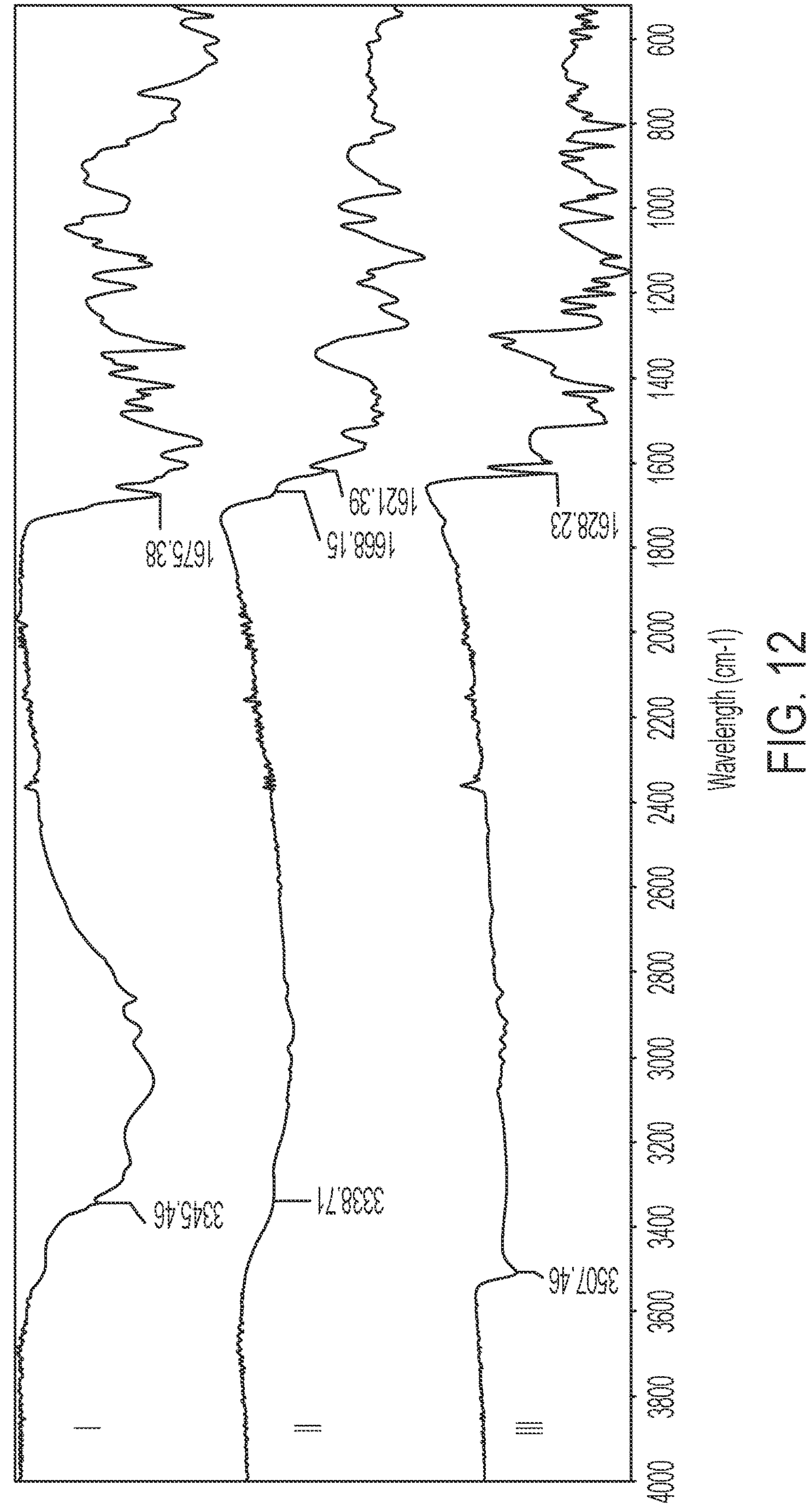
FIG. 12. FT-IR spectrum of: I) L-arginine; II) curcumin and L-arginine co-amorphous 1:1 obtained by flash evaporation in ethanol; and III) highly pure curcumin (C3 complex).
Figure 13:
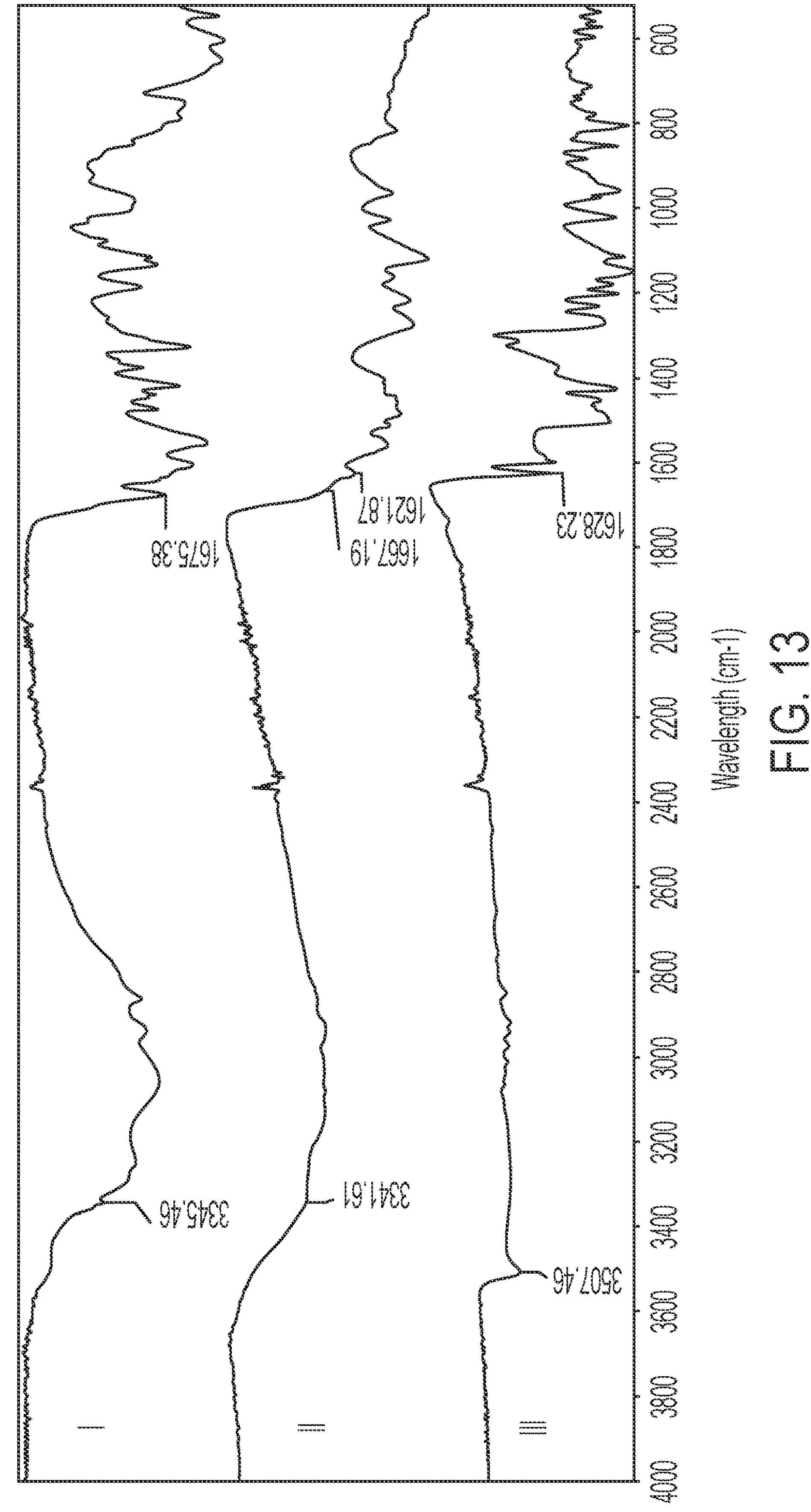
FIG. 13. FT-IR spectrum of: I) L-arginine; II) curcumin and L-arginine co-amorphous 1:2 obtained by flash evaporation in ethanol; and III) high purity curcumin (C3 complex).
Figure 14:
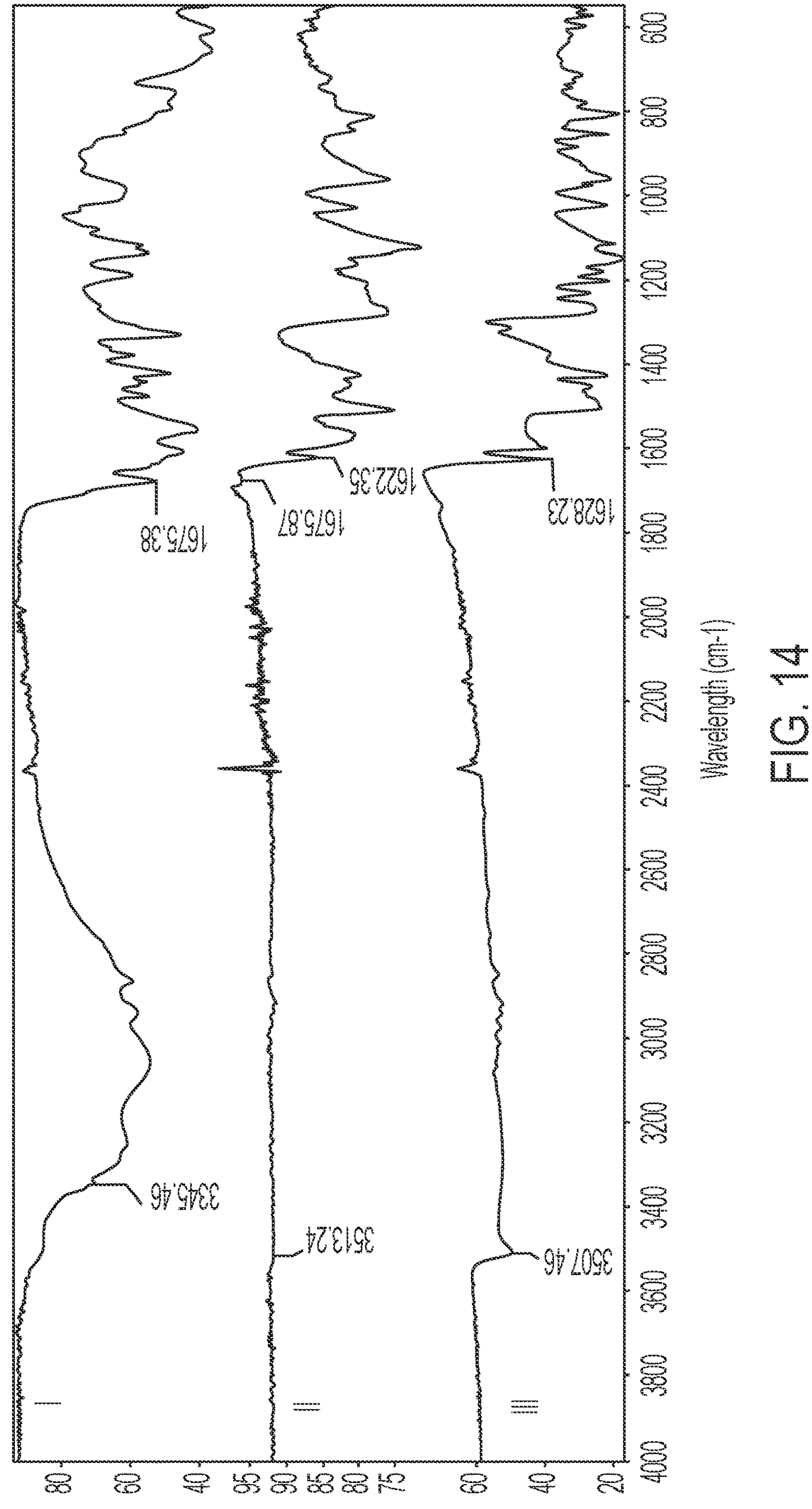
FIG. 14. FT-IR spectrum of: I) L-arginine; II) curcumin and L-arginine co-amorphous 2:1 obtained by flash evaporation in ethanol; and III) high purity curcumin (C3 complex).

FIGS. 12 to 14 show the FT-IR spectra obtained for the co-amorphous phases of curcumin and L-arginine 1:1, 1:2 and 2:1, respectively. Important changes are observed in the O—H and N—H vibration zone corresponding to the hydroxyl and amino groups of L-arginine (from 3510 to 3049 $cm^{-1}$), which means that the hydroxyl groups of curcumin interact with the amine group of arginine.

The H—O stretching band of the initial curcumin shows a well-defined band at 3507 $cm^{-1}$, which disappears completely in the curcumin and L-arginine co-amorphous phases, indicating that the hydroxyl groups of curcumin do not form an important interaction in the curcumin raw material, and the hydroxyl groups of curcumin, in the presence of L-arginine, establish an important interaction with the amino groups of L-arginine. The displacements of the carbonyl bands are shown in Table 1.

TABLE 1

Displacements ($cm^{-1}$) of carbonyl bands in the amorphous NSF.

| Phase | v C═O curcumin | v C═O co-former |
|---|---|---|
| Curcumin | 1628 | — |
| L-arginine | — | 1675 |
| Curcumin and L-arginine 1:1 | 1621 | 1668 |
| Curcumin and L-arginine 1:2 | 1621 | 1667 |
| Curcumin and L-arginine 2:1 | 1622 | 1675 |

Curcumin carbonyl groups (C═O) show a well-defined band at 1628 $cm^{-1}$, which is not importantly shifted in the IR spectra obtained for the phases of curcumin and L-arginine 2:1, 1:1 and 1:2 (FIGS. 12, 13 and 14, respectively), shifting to 1621 $cm^{-1}$. Possibly, this indicates that the interaction pattern established by the carbonyl groups in the initial curcumin remains unchanged when the co-amorphous phase with L-arginine is formed.

The band assigned to the C═O bond vibration of the carboxylic acid of L-arginine appears at 1675 $cm^{-1}$. For the phases 1:1 (FIG. 13) and 1:2 (FIG. 14), the band appears at 1668 and 1667 $cm^{-1}$ respectively. In the case of the phase 2:1, a shift of the C═O band of the carboxylic acid in L-arginine is not observed, which could be attributed to the fact that there is no significant interaction with curcumin.

It is important to mention that no intense and well-defined bands are observed between 1500 and 1600 $cm^{-1}$, which are indicative of the formation of carboxylate ions in the arginine salt, so we can conclude that no proton transfer takes place from the co-former to the drug and that they are co-amorphous phases.

Characterization of NSF of Curcumin and L-Arginine, by Obtaining the Respective DSC and TGA Thermograms.

Figures 15, 16:
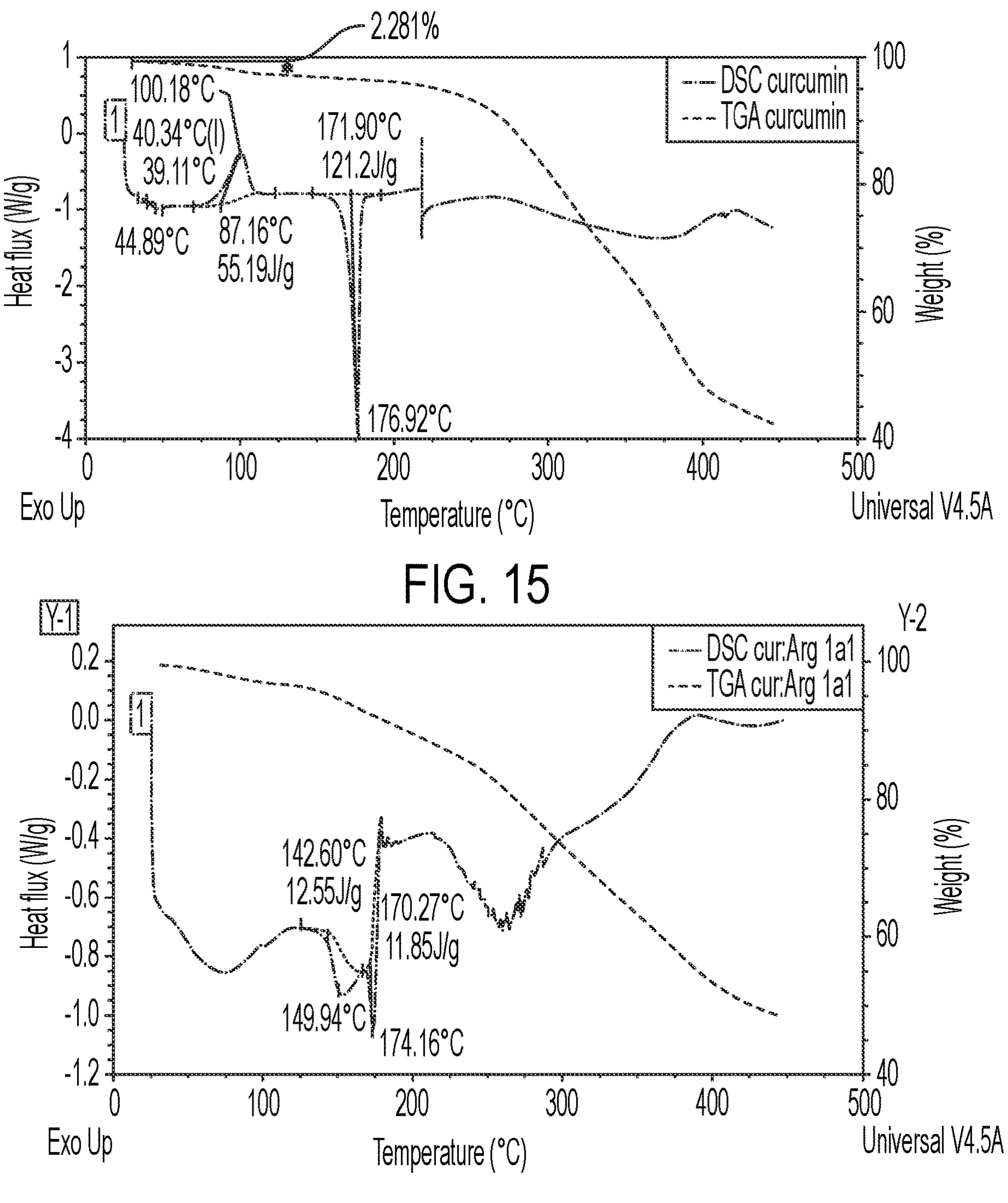
FIG. 15. DSC-TGA thermogram of the amorphous curcumin obtained by flash evaporation in ethanol.
FIG. 16. DSC-TGA thermogram of curcumin and L-arginine co-crystal 1:1 obtained by mechanochemical reaction in water.

FIG. 15 shows a DSC-TGA thermogram of amorphous curcumin obtained by flash evaporation in ethanol.

FIG. 16 corresponds to the DSC-TGA thermogram of the co-crystalline phase obtained by mechanochemical reaction of curcumin and L-arginine 1:1 in water.

Figures 17, 18:
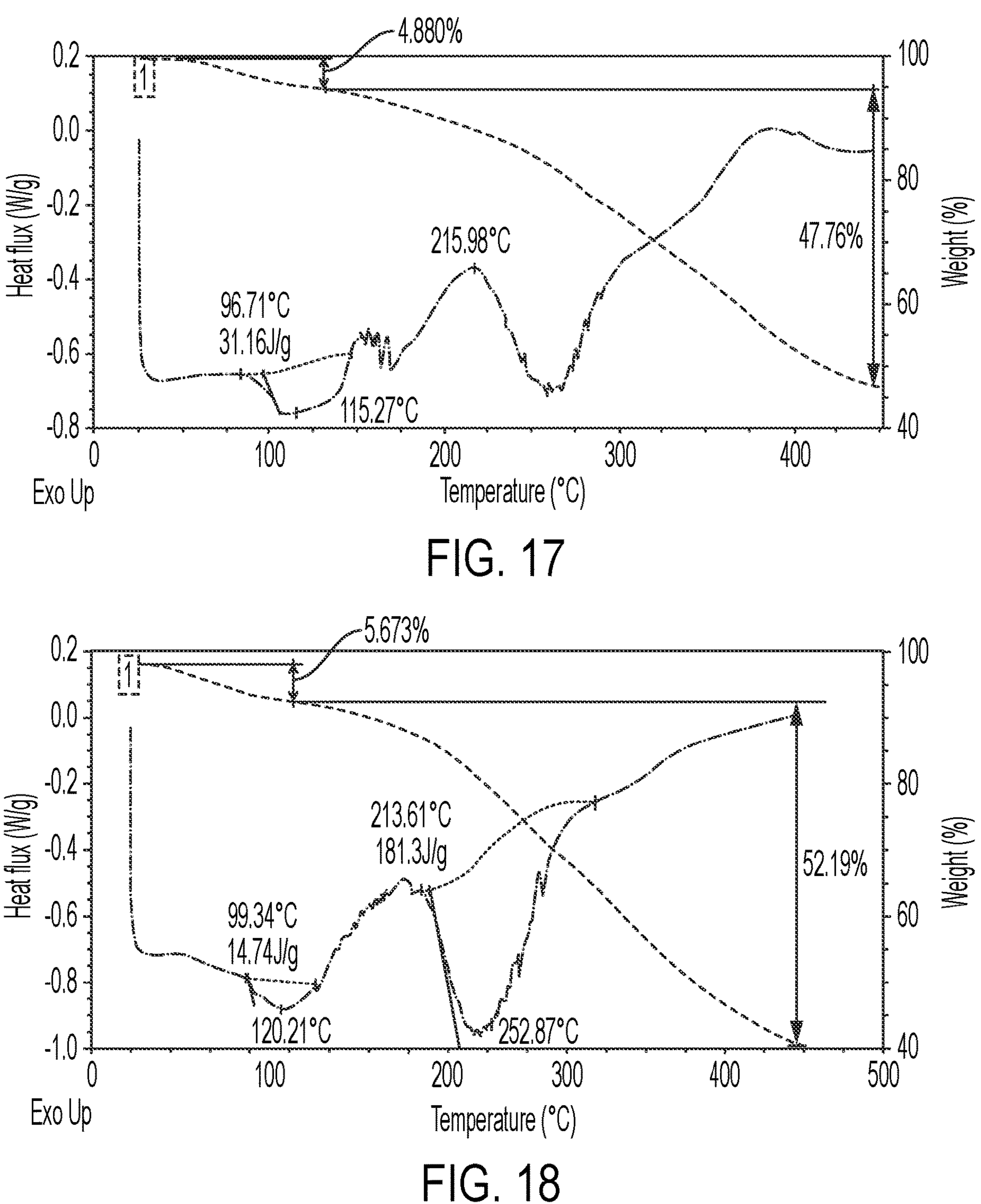
FIG. 17. DSC-TGA thermogram of the co-amorphous phase of curcumin and L-arginine 1:1 obtained by flash evaporation in ethanol.
FIG. 18. DSC-TGA thermogram of the co-amorphous phase of curcumin and L-arginine 1:2 obtained by flash evaporation in ethanol.
Figure 19:
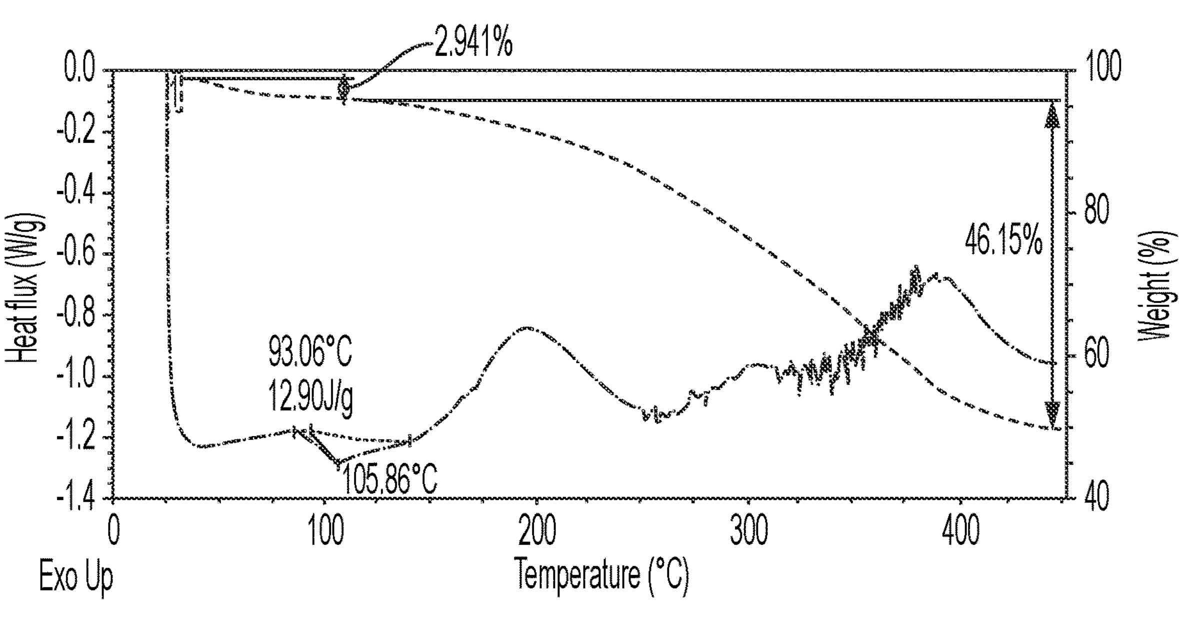
FIG. 19. DSC-TGA thermogram of the co-amorphous phase of curcumin and L-arginine 2:1 obtained by flash evaporation in ethanol.

FIGS. 17 to 19 show DSC and TGA thermograms of the curcumin and L-arginine co-amorphous form in the ratios 1:1, 1:2 and 2:1. In all of the obtained phases, an endothermic event between 93 and 100° C. is observed, which according to the TGA is associated to dehydration of the phases with weight losses ranging from 3 to 5%, which correspond to 1.5 or 2 moles of water contained in the phases, concluding that they are hydrated co-amorphous phases.

After dehydration, at approximately 140° C., a possible exothermic event is observed in the DSC, which could be attributed to crystallization. However, the TGA shows another mass loss of the compound starting at such temperature. This can be attributed to the fact that at 140° C. the co-amorphous form begins to decompose, curcumin sublimes (melting point 183° C.), and arginine crystallizes and finally sublimes at approximately 250° C. (melting point of arginine 260° C.)

Characterization of the Co-Amorphous Phases by Determining the Density of the Obtained Solids.

We determined densities of the obtained solids, resulting in an insignificant increase in density. See Table 2.

TABLE 2

Density values of the obtained co-amorphous phases. Densities in g/cm$^3$

| Phase | | Determination 1 | Determination 2 | Determination 3 | Average |
|---|---|---|---|---|---|
| Curcumin | Density | 1.3688 | 1.3698 | 1.3575 | 1.3653 |
| | Std. Dev. | 0.0037 | 0.0038 | 0.0075 | 0.005 |
| Cur and L-Arg 1:1 | Density | 1.4966 | 1.4762 | 1.4982 | 1.4903 |
| | Std. Dev. | 0.0063 | 0.0142 | 0.0079 | 0.0094 |
| Cur and L-Arg 1:2 | Density | 1.4181 | 1.4176 | 1.4078 | 1.4145 |
| | Std. Dev. | 0.0036 | 0.0031 | 0.0067 | 0.0044 |
| Cur and L-Arg 2:1 | Density | 1.5427 | 1.5755 | 1.5497 | 1.5559 |
| | Std. Dev. | 0.0133 | 0.0195 | 0.0063 | 0.0130 |

Accelerated Stability, Solubility and Dissolution Tests

Figure 20:
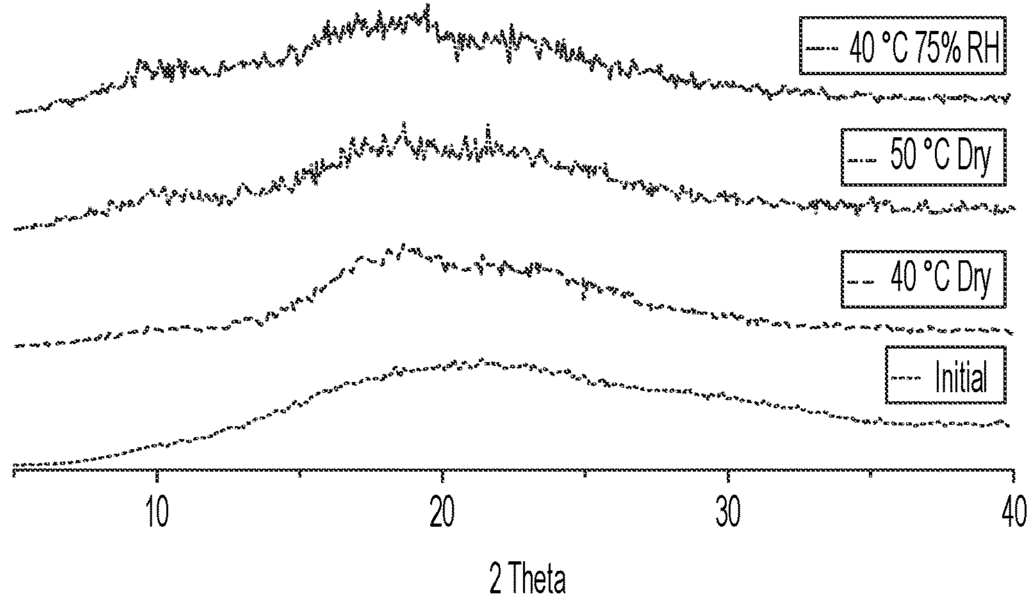
FIG. 20. Powder diffraction pattern obtained from accelerated stability tests at 40° C. and 50° C. under dry conditions and at 40° C. with 75% relative humidity for the co-amorphous of curcumin and L-arginine 1:1.
Figure 21:
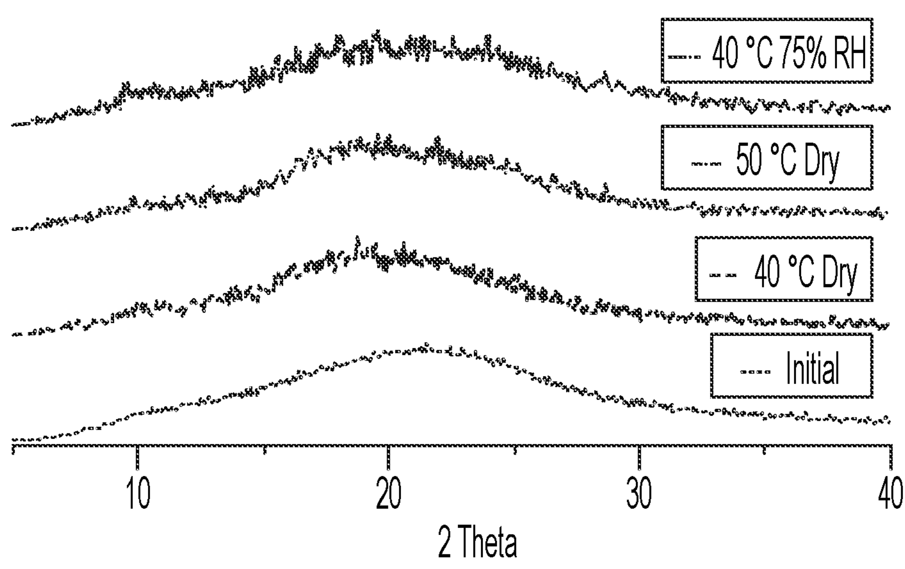
FIG. 21. Powder diffraction pattern obtained from accelerated stability tests at 40° C. and 50° C. under dry conditions and at 40° C. with 75% relative humidity for the co-amorphous of curcumin and L-arginine 1:2.
Figure 22:
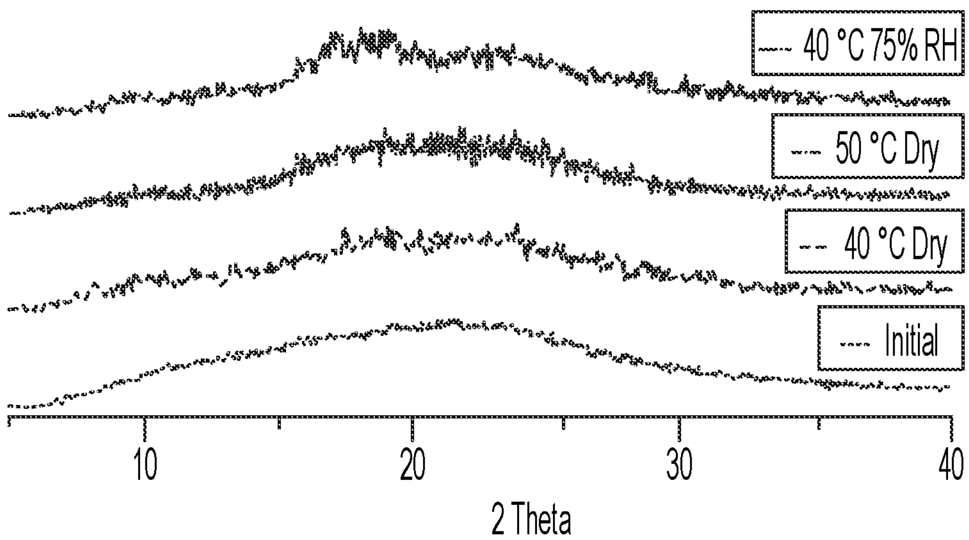
FIG. 22. Powder diffraction pattern obtained from accelerated stability tests at 40° C. and 50° C. under dry conditions and at 40° C. with 75% relative humidity for the co-amorphous of curcumin and L-arginine 2:1.

Accelerated stability studies were carried out by leaving the co-amorphous phases samples 1 month at 40° C. and 50° C. with 0% humidity and 40° C. with 75% RH. Subsequently, the samples were characterized by X-ray diffraction and compared with the respective initial phases and raw materials. FIGS. 20 to 22 show the diffractograms of the different co-amorphous phases subjected to the indicative stability test, showing that the phases are stable at 40 and 50° C. under dry conditions.

Figures 23, 24:
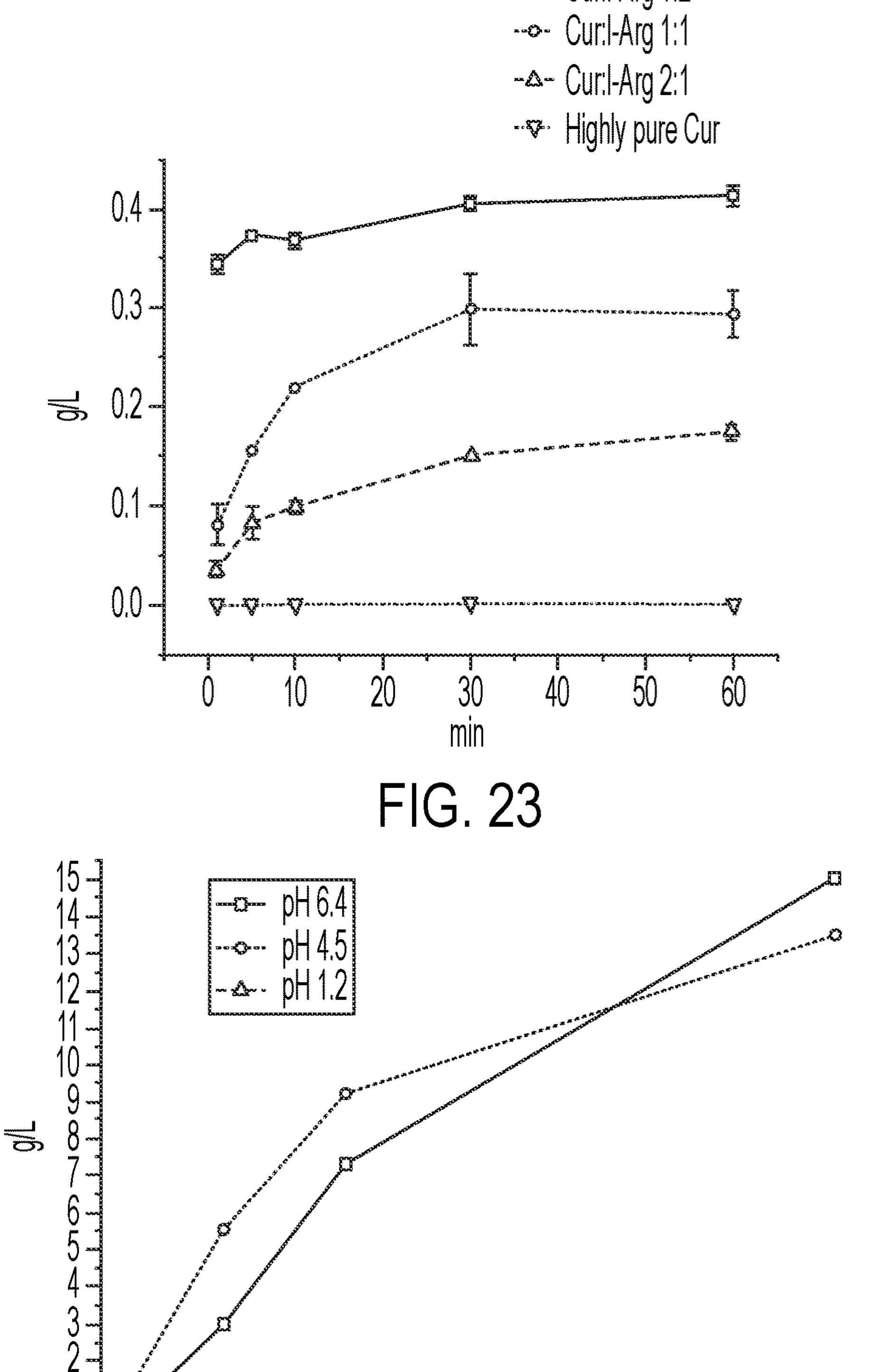
FIG. 23. Solubility profile of co-amorphous forms of curcumin and L-arginine at different stoichiometries: a) 1:2, b) 1:1 and c) 2:1; as well as d) high purity curcumin (C3 complex) using water as dissolution medium and a temperature of 37.5° C.
FIG. 24. Solubility profile of co-amorphous form of curcumin and L-arginine 1:2 using as dissolution media HCl buffer at pH 1.2, acetate buffer at pH 4.5 and phosphate buffer at pH 6.8.

FIG. 23 shows the solubility profile of the co-amorphous forms of curcumin and L-arginine, a) 1:2, b) 1:1, c) 2:1 and d) high purity commercial curcumin (C3 complex) using water as dissolving medium at a temperature of 37.5° C. It is clearly observed that the phase of curcumin and L-arginine 1:2 has the highest solubility in water and at a temperature of 37.5° C., reaching a solubility of 350 to 400 mg per liter. The phases 1:1 and 2:1 achieved solubilities of 250 and 150 mg per liter, respectively. In addition to the above, high purity commercial curcumin did not solubilize at least under these conditions.

We carried out stability tests at physiologically relevant pH values.

FIG. 24 shows the solubility data of the phase of curcumin and L-arginine 1:2 employing dissolution medium of HCl buffer pH 1.2, acetate buffer pH 4.5 and phosphate buffer pH 6.8. Results show that the phase of curcumin and L-arginine 1:2 has low solubility in highly acidic media, such as HCl buffer pH 1.2. However, a good solubility is observed in acetate (pH 4.5) and phosphate (pH 6.8) buffers, in which a solubility of 13-15 g/L is reached at 30 minutes.

FIG. 23 shows a marked increase in the water solubility of the three co-amorphous phases with respect to curcumin alone.

Thermodynamic Solubility Studies

This test shows the equilibrium between the liquid phase corresponding to the saturated solution and the solid phase corresponding to the undissolved drug. It was performed by adding 2 g of the solid phase to LSS (sodium lauryl sulfate) medium, with stirring at 37.5° C., and taking aliquots at 3, 5, 10 and 30 minutes. Aliquots were filtered and measurements were made with UV-Vis spectroscopy at 420 nm. Due to the poor solubility of curcumin in water, the molar absorptivity coefficient was calculated in water with 1% LSS.

High concentration samples of the curcumin and L-arginine co-amorphous phases, curcumin lecithin liposomes (INDENA), high purity commercial sample (Complex C3) and a compound curcumin:L-lysine, were tested in water with 1% LSS.

It comes evident that the curcumin and L-arginine co-amorphous solids with stoichiometry 1:1 and 2:1 show a considerable increase in the solubility of curcumin, reaching values of 3.2 and 4.0 g/L, respectively.

Of all phases, curcumin and the compound curcumin:L-lysine show the lowest solubilities, solubilizing 0.11 and 0.34 g/L at 30 min.

It is important to mention that the solubility of curcumin alone could not be determined because it is almost insoluble in water.

We measured the solubility of the co-amorphous phases at a lower concentration of 0.05 g in 3.5 ml, for determining the effect of concentration on the aggregation phenomenon. This resulted in a decreased solubility because the amount required to saturate the phase was much lower. However, at low concentrations, the aggregation phenomenon was completely inhibited, and no reprecipitation was observed.

Permeability Studies

Permeability studies were carried out using pig membranes and water as dissolution medium. Diffusion profiles were obtained by plotting accumulated mg of drug vs time (h). The flux was obtained by using the formula J=Q/(A*t) where Q is the amount of drug that passes through the membrane, in accumulated mg; A is the exposed area of the membrane in cm$^2$; and t is the time at which the measurement was made; the flux profile was obtained by plotting the flow (mg accum cm$^{-2}$ t$^{-1}$) vs time (h).

Figure 25:
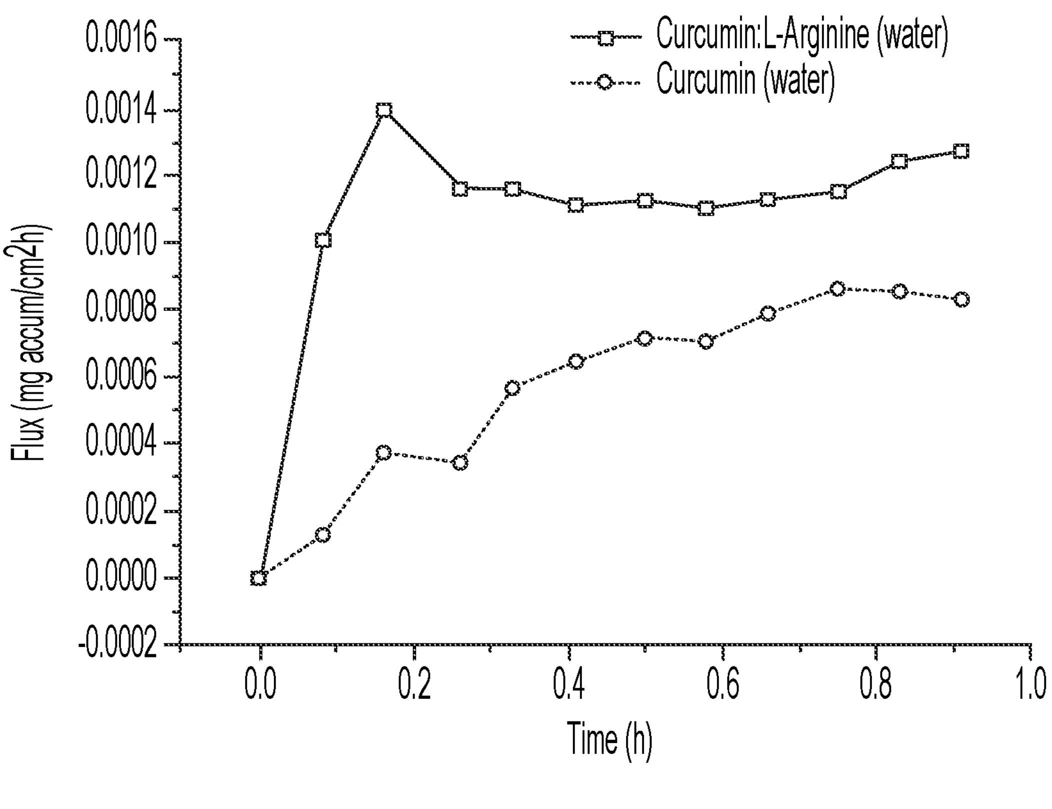
FIG. 25. Diffusion profiles obtained from permeability studies in water using pig membranes, for curcumin and the co-amorphous phase of curcumin and L-arginine 1:2.

FIG. 25 shows the flow profile for curcumin and the phase of curcumin and L-arginine 1:2, using water as the diffusion medium. The graph shows a flow increase for the phase of curcumin and L-arginine 1:2, reaching its maximum flow at 10 min, and then reaching the stationary state. In contrast, regarding curcumin, it can be observed that the flow continues to increase until 45 min, then enters the stationary state.

This flow increase for the phase of curcumin and L-arginine 1:2 can be attributed to an increase of the solubility of the phase of curcumin and L-arginine 1:2 in water; since it is higher than curcumin, there is a greater amount of curcumin present in the medium, to permeate. In contrast, the solubility of curcumin in water is very low, thus the concentration of curcumin in water solution, which can permeate through the membrane, is almost insignificant.

As a result of these tests, the graphs in FIGS. 1-10 show that the co-amorphous form of curcumin and L-arginine has a surprising anti-inflammatory and/or antiallodynic effect; in addition, we demonstrated the existence of a compound formed by curcumin and arginine, which is stable (FIGS. 11-19); said compound confers different properties with respect to those exhibited by the initial components, reflecting an outstanding increase in solubility and permeability (FIGS. 23, 24 and 25).

The curcumin+L-arginine combination is administered in different compositions. It can be in the form of a suspension, pill, tablet, granulate, powder, capsule, semi-solid, ointment, cream or liquid.

A design of the solid composition can be as a tablet, pill, granulate, dragée, powder or powder for reconstituting a solution, and where appropriate, it may contain compressibility vehicle, binder, diluent, antistatic, lubricant, plasticizer and disintegrant in a compartment separated from the final outer layer. An insulating layer or coating is added on the active layer, such insulating layer is made up of a coating polymer that confers protection from factors such as humidity, light, among others.

The present invention additionally refers to a new co-amorphous form of curcumin and L-arginine with improved properties and compositions containing said form, and the process of making the composition and its use.

The new solid form has improved chemical, biological or physical properties, such as enhanced solubility, dissolution rate, bioavailability, pharmacokinetics, mechanical resistance, flow properties, particle size, melting point, among others.

A co-crystal is a crystalline solid formed by an active ingredient and a co-former, both of which are found in the same crystal cell. A co-amorphous form is a solid made up of an active ingredient and a co-former, which exist in a disordered molecular arrangement.

Methods for identifying a solid form, and distinguishing a co-crystal from a co-amorphous from, include X-ray Powder Diffraction (XRPD) analysis, Fourier Transform Infrared Spectrometry (FT-IR), and Differential Scanning calorimetry—Thermogravimetric Analysis (DSC-TGA).

The present invention provides the solid form of curcumin and arginine in different molar proportions or stoichiometric ratios selected from the group consisting of (1:1), (1:2), (2:1), (1:3) and (3:1).

The method used to prepare the solid form is selected from the group consisting of slurry, flash evaporation, and mechanochemical reaction. The solvent may be any solvent capable of dissolving the curcumin and the co-former. Preferably, a solvent having a non-toxic or low toxicity effect on the organism and/or a solvent which is easily evaporated, such as water or ethanol, is used.

In one embodiment, the condition or disease that can be treated by the methods of the present invention, or the uses of the present invention, can be any disease or condition that is treatable with an antitumor agent, an anticancer agent, an antioxidant, an anti-arthritic agent, a neuroprotective agent, an anti-inflammatory agent, an antiviral agent or an anti-infective.

In one embodiment, the pharmaceutical composition of the present invention comprises an amount of the solid form of curcumin and arginine that represents from about 90% to about 1%, by weight, based on the total weight of the composition.

In certain embodiments, the pharmaceutical composition may be presented in an appropriate dosage form. For example, the pharmaceutical composition may be suitable for tablets, powders, capsules, pills, liquids, syrups, suspensions, emulsions, elixirs, drops, ointments, gels, transdermal patches, parenteral dosage forms, and oral solution forms.

The invention claimed is:

1. A solid coamorphous compound, comprising:

curcumin and arginine compounds, wherein these compounds interact by non-covalent bonds, and are present in a molar ratio of curcumin to L-arginine of 1:2, 1:1 or 2:1.

2. A composition comprising:

the solid coamorphous compound of curcumin and arginine according to claim 1; and one or more pharmaceutical excipients.

3. A solid coamorphous compound comprising:

curcumin and L-arginine, wherein these compounds interact by non-covalent bonds, and are present in a molar ratio of curcumin to L-arginine from 1:2 to 2:1.

4. A composition comprising the solid coamorphous compound as claimed in claim 3; and one or more pharmaceutical excipients.

* * * * *